US008536221B2

(12) United States Patent
Mortell et al.

(10) Patent No.: US 8,536,221 B2
(45) Date of Patent: Sep. 17, 2013

(54) AMIDE DERIVATIVES AS POSITIVE ALLOSTERIC MODULATORS AND METHODS OF USE THEREOF

(75) Inventors: Kathleen H. Mortell, Chicago, IL (US); Diana L. Nersesian, Gurnee, IL (US); Michael R. Schrimpf, Grayslake, IL (US); Chih-Hung Lee, Vernon Hills, IL (US); Murali Gopalakrishnan, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 752 days.

(21) Appl. No.: 12/367,096

(22) Filed: Feb. 6, 2009

(65) Prior Publication Data

US 2009/0270408 A1 Oct. 29, 2009

Related U.S. Application Data

(60) Provisional application No. 61/143,628, filed on Jan. 9, 2009, provisional application No. 61/026,886, filed on Feb. 7, 2008.

(51) Int. Cl.
*A01N 43/30* (2006.01)
*A61K 31/36* (2006.01)
*C07D 209/44* (2006.01)

(52) U.S. Cl.
USPC .......................... 514/464; 548/469; 548/470

(58) Field of Classification Search
USPC ................................ 548/469, 470; 514/464
See application file for complete search history.

(56) References Cited

U.S. PATENT DOCUMENTS

| 2004/0204409 A1 | 10/2004 | Ando et al. |
| 2005/0065178 A1 | 3/2005 | Basha et al. |
| 2005/0137204 A1 | 6/2005 | Ji et al. |
| 2005/0245531 A1 | 11/2005 | Ji et al. |
| 2006/0106011 A1 | 5/2006 | Bock et al. |
| 2009/0291963 A1 | 11/2009 | Schadt et al. |

FOREIGN PATENT DOCUMENTS

| WO | 9721707 A1 | 6/1997 |
| WO | 0112187 | 2/2001 |
| WO | 0115686 A1 | 3/2001 |
| WO | 03087086 A2 | 10/2003 |
| WO | 2004029053 | 4/2004 |
| WO | 2006060737 A2 | 6/2006 |
| WO | 2008019357 | 2/2008 |

OTHER PUBLICATIONS

Adler, L.E., et al., Schizophrenia Bull., vol. 24 pp. 189-202 (1998).
Albuquerque, E.X., et al., Alzheimer Dis. Assoc. Disord., vol. 15 Suppl. 1 pp. S19-S25 (2001).
Alkondon, M., et al., Prog. Brain Res., vol. 145 pp. 109-120 (2004).
Balbani, A.P.S., et al., Exp. Opin. Ther. Patents, vol. 13 pp. 287-297 (2003).
Bitner, R.S., et al., J. Neuroscience, vol. 27 (39) pp. 10578-10587 (2007).
Bolton, R.E., et al., J. Chem. Soc. Chem. Commun., pp. 1775, (1999).
Briggs, C.A., et al., Neuropharmacology, vol. 34 pp. 583-590 (1995).
Briggs, C.A., et al., Neuropharmacology, vol. 37 pp. 1095-1102 (1998).
Broad, L.M., et al., Drugs of the Future, vol. 32 (2) pp. 161-170 (2007).
Bunnelle, W.H., et al., Exp. Opin. Ther. Patents, vol. 13 (7) pp. 1003-1021 (2003).
Carreño, M.C., et al., Org. Lett., vol. 6 pp. 297-299 (2004).
Charette, A.B., et al., Synlett, pp. 1779-1782 (2005).
Cordero-Erausquin, M., et al., Proc. Nat. Acad. Sci., vol. 98 pp. 2803-2807 (2001).
Couturier, S., et al., Neuron, vol. 5 pp. 847-856 (1990).
Dajas-Bailador, F., et al., Trends Pharmacol. Sci., vol. 25 pp. 317-324 (2004).
Decker, M.W., et al., Exp. Opin. Ther. Patents, vol. 10 (10) pp. 1819-1830 (2001).
Decker, M.W., et al., Curr. Top. Med. Chem., vol. 4 pp. 369-384 (2004).
De Luca, V., et al., Acta Psychiatr. Scand., vol. 114 pp. 211-115 (2006).
D'Andrea, M.R., et al., Curr. Pharm. Des., vol. 12 pp. 677-684 (2006).
Faghih, R., et al., Recent Patents on CNS Drug Discovery, vol. 2 (2) pp. 99-106 (2007).
Fang, G.H., et al., Org. Lett., vol. 6 pp. 357-360 (2004).
Feuerbach, D., et al., Neuropharmacology, vol. 56 pp. 254-263 (2009).
Friedman, J.I., Biol. Psychiatry, vol. 51 pp. 349-357 (2002).
Furniss, B.S., et al., "Vogel's Textbook of Practical Organic Chemistry", Longman Scientific & Technical, 5th Edition, Essex SM20 2JE, England (1989).
Gotti, C. et al., Prog. Neurobiol., vol. 74 pp. 363-396 (2004).
Gotti, C., et al., Curr. Pharm. Des., vol. 12 pp. 407-428 (2006).
Greene, et al., Protective Groups in Organic Synthesis, Wiley & Sons (1999).
Gundish, D., Expert Opin. Ther. Patents, vol. 15 (9) pp. 1221-1239 (2005).
Gurwitz, D., Exp. Opin. Invest. Drugs, vol. 8 (6) pp. 747-760 (1999).
Hajos, M., et al., J. Pharmacol. Exp. Ther., vol. 312 pp. 1213-1222 (2005).
Hevers, W., et al., Mol. Neurobiol., vol. 18 pp. 35-86 (1998).
Higuchi, T., et al., Prodrugs as Novel Delivery Systems, A.C.S. Symposium Series, vol. 14, (2004).
Hogg, R.C., et al., Rev. Physiol., Biochem., vol. 147 pp. 1-46 (2003).
Hunter, B.E., et al., Neurosci. Lett., vol. 168 pp. 130-134 (1994).
Hurst, R.S., et al., J. Neurosci., vol. 25 pp. 4396-4405 (2005).
Illi, V.O., et al., Synthesis, pp. 387-388 (1979).
IUPAC1974 Recommendations for Section E, Fundamental Steochemitrypure Appl. Chem., vol. 45 pp. 13-30 (1976).
Jonnala, R.B., et al., J. Neurosci. Res., vol. 66 pp. 565-572 (2001).

(Continued)

*Primary Examiner* — Paul V. Ward
(74) *Attorney, Agent, or Firm* — Lisa V. Mueller; Michael Best & Friedrich LLP

(57) ABSTRACT

The invention relates to novel amide derivatives that are PAMs of neuronal nicotinic receptors, compositions comprising the same, processes for preparing such compounds, and methods for using such compounds and compositions.

5 Claims, 3 Drawing Sheets

(56) References Cited

OTHER PUBLICATIONS

Keller, J.J., et al., Behav. Brain Res., vol. 162 pp. 143-152 (2005).
Kihara, T., et al., J. Biol. Chem., vol. 276 pp. 13541-13546 (2001).
Konno, S., et al., Heterocycles, vol. 34 pp. 225-228 (1992).
Korolkovas, A., et al, "Essentials of Medicinal Chemistry", pp. 97-118, (1998).
Leonard, S., et al., Eur. J. Biol. Chem., vol. 276 pp. 13541-13546 (2001).
Levin, E.D., et al., J. Neurobiol., vol. 53 pp. 633-640 (2002).
Ley, S.V., et al., Angew. Chem. Int. Ed., vol. 42 pp. 5400-5449 (2003).
Liu, Q.S., et al., PNAS., vol. 98 pp. 4734-4739 (2001).
Martin, L.F., et al., Psychopharmacology (Berl), vol. 174 pp. 54-64 (2004).
Naruto, S., et al., Chem. Pharm. Bull., vol. 20 (10) pp. 2163-2171 (1972).
Paterson, D. et al., Prog Neurobiol., vol. 61 pp. 75-111 (2000).
Pichat, P., et al., Society for Neuroscience Abstract, No. 583.3 (2004).
Prakash, G.K.S., et al., Chem. Rev. vol. 97 pp. 757-786 (1997).
Prescott, E., et al., Methods in Cell Biology, vol. 14 p. 33, Academic Press, New York City, N.Y., (1976).
Roche, E.B., et al., Bioreversible Carriers in Drug Design, American Pharmaceutical Association, Pergamon Press (1987).
Romanelli, M.N., et al., Exp. Opin. Ther. Patents, vol. 17 (11) pp. 1365-1377 (2007).
Rowley, M., et al., J. Med. Chem., vol. 44 pp. 477-501 (2001).
Shimohama, S., et al., Brain Res., vol. 779 pp. 359-363 (1998).
Stevens, K.E., et al., Psychoparmacology, vol. 136 pp. 320-327 (1998).
Trumbull, J.D., et al., High throughput electrophysiology using a fully automated, multiplexed recording system, Receptors Channels, vol. 9 pp. 19-28 (2003).
Van Kampen, M., et al., Psychopharmacology (Berl), vol. 172 pp. 375-383 (2004).
Vincler, M. et al., Exp. Opin. Ther. Targets, vol. 11 (7) pp. 891-897 (2007).
Vincler, M., et al., Exp. Opin. Invest. Drugs, vol. 14 (10) pp. 1191-1198 (2005).
Wang, H., et al., Nature, vol. 421 pp. 384-388 (2003).
Wallace, D.J., et al., Tetrahedrom Lett., vol. 43 pp. 6987-6990 (2002).
International Search Report dated Sep. 17, 2009.
Bodanszky, et al., The Practice of Peptide Synthesis, Second Revised Edition, Springer-Verlag Berlin Heidelberg Publishers, 1984, Table of Contents.

AMIDE DERIVATIVES AS POSITIVE ALLOSTERIC MODULATORS AND METHODS OF USE THEREOF

This application claims priority to U.S. Provisional Application Ser. No. 61/143,628, filed Jan. 9, 2009, and U.S. Provisional Application Ser. No. 61/026,886, filed Feb. 7, 2008, which are incorporated herein by reference.

TECHNICAL FIELD

The invention relates to novel amide derivatives that are positive allosteric modulators of neuronal nicotinic receptors, compositions comprising the same, and methods for using such compounds and compositions.

DESCRIPTION OF RELATED TECHNOLOGY

Nicotinic acetylcholine receptors (nAChRs) belong to the super family of ligand gated ion channels (LGIC), and gate the flow of cations, controlled by acetylcholine (ACh). The nAChRs can be divided into nicotinic receptors of the muscular junction (NMJ) and neuronal tAChRs or neuronal nicotinic receptors (NNRs). The NNRs are widely distributed throughout the central nervous system (CNS) and the peripheral nervous system (PNS). The NNRs are understood to play an important role in regulating CNS function and the release of many neurotransmitters, for example, ACh, norepinephrine, dopamine, serotonin, and GABA, among others, resulting in a wide range of physiological effects.

Sixteen subunits of nAChRs have been reported to date, which are identified as α2-α10, β1-β4, γ, δ, and ε. Of these subunits, nine subunits, α2 through α7 and β2 through β4, prominently exist in the mammalian brain. Multiple functionally distinct nAChR complexes also exist, for example five α7 subunits can form a receptor as a homomeric functional pentamer or combinations of different subunits can complex together as in the case of α4β2 and α3β4 receptors (Vincler, M., et al., *Exp. Opin. Ther. Targets*, 2007, 11 (7): 891-897; Paterson, D. et al., *Prog. Neurobiol.* 2000, 61: 75-111; Hogg, R. C., et al., *Rev. Physiol., Biochem. Pharmacol.*, 2003, 147: 1-46; Gotti, C., et al., *Prog. Neurobiol.*, 2004, 74: 363-396).

The homomeric α7 receptor is one of the most abundant nicotinic receptors, along with α4β2 receptors, in the human brain, wherein it is heavily expressed in the hippocampus, cortex, thalamic nuclei, ventral tegmental area and substantia nigra (Broad, L. M., et al., *Drugs of the Future*, 2007, 32(2): 161-170).

The role of α7 NNRs in neuronal signaling in the CNS also has been actively investigated (Couturier, S., et al., *Neuron*, 1990, 5: 847-56). The α7 NNRs have been demonstrated to regulate interneuron excitability, modulate the release of excitatory and inhibitory neurotransmitters, and lead to neuroprotective effects in experimental in vitro models of cellular damage (Alkondon, M. et al., *Prog. Brain Res.*, 2004, 145: 109-20).

Biophysical studies have shown that α7 subunits, when expressed in heterologous expression systems, activate and desensitize rapidly, and furthermore, exhibit relatively higher calcium permeability compared to other NNR combinations (Dajas-Bailador, F., et al., *Trends Pharmacol. Sci.*, 2004.25: 317-24).

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence (Keller, J. J., et al., *Behav. Brain Res.*, 2005, 162: 143-52; Gundish, D. *Expert Opin. Ther. Patents*, 2005, 15 (9): 1221-1239; De Luca, V., et al., *Acta Psychiatr. Scand.*, 2006, 114: 211-5).

More particularly, the α7 NNRs have been linked to conditions and disorders related to attention deficit disorder, ADHD, AD, mild cognitive impairment (MCI), senile dementia, dementia associated with Lewy bodies, dementia associated with Down's syndrome, AIDS dementia, Pick's disease, as well as cognitive deficits associated with schizophrenia (Martin, L. F., et al., *Psychopharmacology* (Berl), 2004, 174: 54-64, Romanelli, M. N., et al., *Exp. Opin. Ther. Patents*, 2007, 17 (11): 1365-1377). The α7 NNRs have also been reported to slow disease progression in AD (D'Andrea, M. R., et al., *Curr. Pharm. Des.*, 2006, 12: 677-84).

Accordingly, modulating the activity of α7 NNRs demonstrates promising potential to prevent or treat a variety of diseases indicated above, such as AD, other dementias, schizophrenia and neurodegeneration, with an underlying pathology that involves cognitive function including, for example, aspects of learning, memory, and attention (Gotti, C., et al., *Curr. Pharm. Des.*, 2006, 12: 407-428).

The NNR ligands have been also implicated in smoking cessation, weight control and as potential analgesics (Balbani, A. P. S., et al., *Exp. Opin. Ther. Patents*, 2003, 13 (7): 287-297; Gurwitz, D., *Exp. Opin. Invest. Drugs*, 1999, 8(6): 747-760; Vincler, M., *Exp. Opin. Invest. Drugs*, 2005, 14 (10): 1191-1198; Bunnelle, W. H., et al., *Exp. Opin. Ther. Patents*, 2003, 13 (7): 1003-1021; Decker, M. W., et al., *Exp. Opin. Invest. Drugs*, 2001, 10 (10): 1819-1830; Vincler, M., et al., *Exp. Opin. Ther. Target.*, 2007, 11 (7): 891-897). Most of the attention with regards to pain relief has gone to the α4β2 subtype (Decker, M. W., et al., *Curr. Top. Med. Chem.*, 4: 369-384, 2004). Although the α7 NNRs have long been recognized for their involvement in the inflammatory response through inhibition of the release of tumor necrosis factor (TNF) and other cytokines (Wang, H. et al *Nature* 421: 384-388, 2003), more recent evidence has pointed to a role for α7 NNRs in pain as well. For instance, a population of α7 NNRs in the spinal cord has been identified that modulates neurotransmission associated with the pain-relieving effects of nicotinic compounds (Cordero-Erausquin, M. et al., *Proc. Val. Acad. Sci. USA* 98:2803-2807, 2001). A selective α7 NNR partial agonist has been reported to show efficacy in models of neuropathic and persistent inflammatory pain (Feuerbach. D. et al., *Neuropharmacology*, 56:254-263, 2009).

Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems. Accordingly, there is a need to identify subtype-selective compounds that embrace the beneficial effects of nicotine, or an NNR ligand, while eliminating or decreasing adverse effects.

Examples of reported NNR ligands, such as PNU-282987 and SSR180711A, are α7 NNR agonists (Hajos, M., et al., *J. Pharmacol. Exp. Ther*, 2005, 312: 1213-22; Pichat, P., et. al., *Society for Neuroscience Abstract*, 2004, number 583.3).

Another compound, AR-R17779, has been reported to improve performance of rats in social recognition, water mazes, or inhibitory avoidance models of cognitive domains (Van Kampen, M., et al., *Psychopharmacology* (Berl), 2004, 172: 375-83). AR-R17779 also reportedly facilitates the induction of hippocampal long term potentiation (LTP) in a proposed cellular model for learning and memory in rats (Hunter, B. E., et al., *Neurosci. Lett.*, 1994, 168: 1304). Compound A-582941, an α7 NNR agonist, has been shown to enhance cognitive performance associated with neurodegenerative diseases such as AD and schizophrenia (Bitner, R. S., et al., *J. Neuroscience*, 2007, 27(39): 10578-10587).

Despite the beneficial effects of NNR ligands, it remains uncertain whether chronic treatment with agonists affecting NNRs may provide suboptimal benefit due to sustained activation and desensitization of the NNR. In contrast to agonists, administering a positive allosteric modulator (PAM) can reinforce endogenous cholinergic transmission without directly simulating the target receptor (see for example, Albuquerque, E. X., et al., *Alzheimer Dis. Assoc. Disord.* 2001, 15 Suppl 1: S19-25). Nicotinic PAMs could selectively modulate the activity of ACh at α7 NNRs. Accordingly, more recently, α7 NNR-selective PAMs have emerged (Faghih, R., et al., *Recent Patents on CNS Drug Discovery*, 2007, 2 (2): 99-106).

Consequently, it would be beneficial to target α7 NNR function by enhancing effects of the endogenous neurotransmitter acetylcholine via PAMs that can reinforce the endogenous cholinergic neurotransmission without directly activating α7 NNRs, like agonists. Indeed, PAMs for enhancing channel activity have been proven clinically successful for $GABA_A$ receptors where benzodiazepines, barbiturates, and neurosteroids behave as PAMs acting at distinct sites (Hevers, W., et al., *Mol. Neurobiol.*, 1998, 18: 35-86).

To date, only a few NNR PAMs are known, such as 5-hydroxyindole (5-HI), ivermectin, galantamine, bovine serum albumin, and SLURP-1, a peptide derived from acetylcholinesterase (AChE). Recently, genistein, a kinase inhibitor was reported to increase α7 responses, and PNU-120596, a urea derivative, was reported to increase the potency and maximal efficacy of ACh as well as improve auditory gating deficits induced by amphetamine in rats. Other NNR PAMs include derivatives of quinuclidine, indole, benzopyrazole, thiazole, and benzoisothiazoles (Hurst, R. S., et al., *J. Neurosci.*, 2005, 25: 4396-4405; Broad, L. M., et al., *Drugs of the Future*, 2007, 32(2):161-170; U.S. Pat. No. 7,160,876).

However, NNR PAMs presently known generally demonstrate weak activity, have a range of non-specific effects, or can only achieve limited access to the central nervous system where α7 NNRs are abundantly expressed.

Accordingly, it would be beneficial to identify and provide new PAM compounds of NNRs and compositions for treating or preventing conditions associated with α7 NNRs. It would further be particularly beneficial if such compounds can provide improved efficacy of treatment while reducing adverse effects associated with compounds targeting neuronal nicotinic receptors by selectively modulating α7 NNRs.

Consequently, the present invention discloses novel amide derivatives that show α7 NNR PAM activity.

SUMMARY OF THE INVENTION

One embodiment relates to compounds of formula (I):

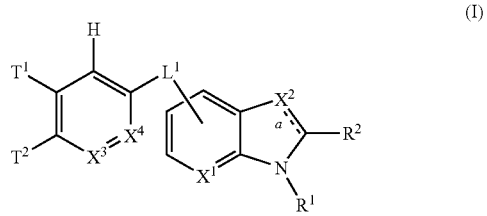

(I)

or a pharmaceutically acceptable salt, ester, amide or prodrug thereof, wherein $R^1$ is alkylcarbonyl, hydrogen, or methyl;
$R^2$ is hydrogen or methyl;
a is a single or double bond;
$X^1$ is N or CH;
$X^2$ is CH when a is a double bond, and $X^2$ is $CH_2$ or —$CH_2CH_2$— when a is a single bond;
$X^3$ and $X^4$ are independently N or CH;
$T^1$ and $T^2$ are independently hydrogen, alkyl, aryl, cycloalkyl, halo, haloalkyl, or $R^3$-$L^2$-, wherein at least one of $T^1$ and $T^2$ is other than hydrogen;
$L^1$ is —C(O)N(H)$CH_2$— or —N(H)C(O)$CH_2$—;
$L^2$ is O or S; and
$R^3$ is alkyl, aryl, cycloalkyl, or haloalkyl.

Another embodiment relates to a method of using compounds of formula (I), formula (II), or formula (III).

Another embodiment is directed to a method of treating conditions and disorders that are regulated by the NNRs using compounds of formula (I), formula (II), or formula (III) or therapeutically effective compositions of compounds of formula (I), formula (II), or formula (III).

Another embodiment is directed to a method of treating a disorder or condition that is modulated by α7 nicotinic acetylcholine receptors in a patient in need of such treatment, comprising administering a therapeutically effective amount of a compound of formula (I), formula (II), or formula (III).

Another embodiment relates to a method of assessing or diagnosing, conditions or disorders related to α7 NNR activity comprising allowing isotope-labeled forms of compounds of formula (I), formula (II), or formula (—III) to interact with cells expressing endogenous α7 NNRs or cells expressing recombinant α7 NNRs and measuring the effects of such isotope-labeled forms of compounds on such cells.

Various aspects also describe the use of NNR ligands, and particularly PAM compounds, to identify other useful target compounds for treating or preventing, or both, diseases or conditions associated with NNR function, in cell-based assays, for example in high-throughput format, using cells or tissues that express native α7 NNR receptors for the purpose of identifying novel α7 NNR agonists or PAMs of the α7 NNR.

DETAILED DESCRIPTION OF THE INVENTION

Definition of Terms

Figure 1:
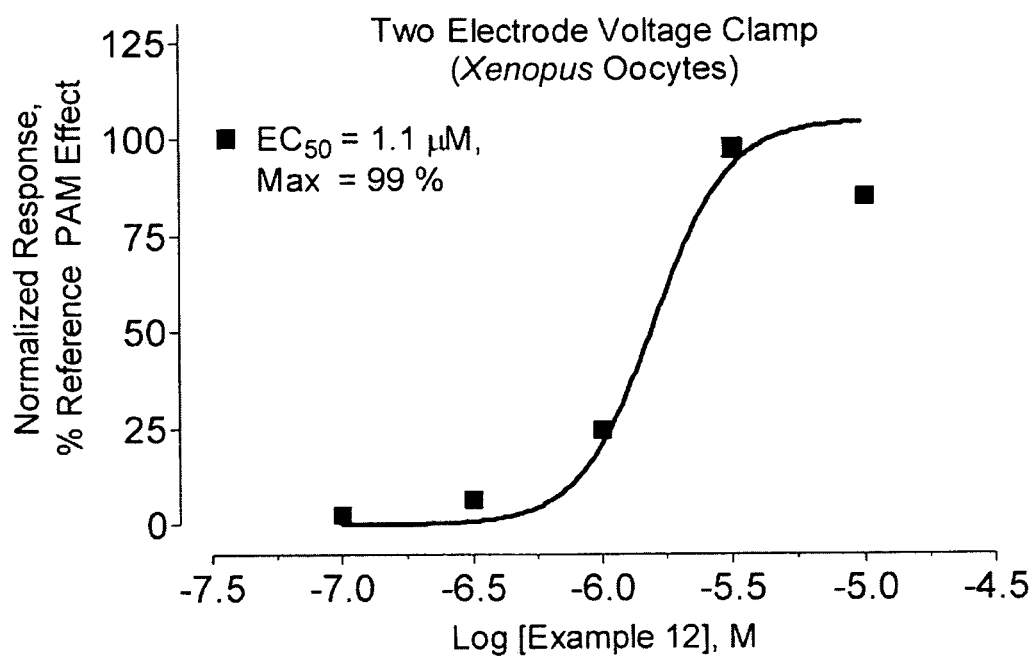
FIG. 1 is a graphical representation of a concentration response curve where submaximum ACh-evoked α7 current potentiation responses are measured in the presence of increasing concentrations of a PAM (Example 12) and normalized to the effect of a reference 10 μM PAM (N'-[(2Z)-3-(2,2-difluoro-1,3-benzodioxol-5-yl)-5-methyl-1,3-thiazol-2 (3H)-ylidene]-N,N-dimethylurea).

Certain terms as used in the specification are intended to refer to the following definitions, as detailed below.

The term "acetyl" means a —C(O)CH$_3$ group.

The term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy tert-butoxy, pentyloxy, hexyloxy and the like.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "amino" refers to —NR$^{90}$R$^{91}$, wherein R$^{90}$ and R$^{91}$ are independently selected from hydrogen and alkyl, as defined herein. Representative examples of amino include, but are not limited to, amino, methylamino, ethylmethylamino, methylisopropylamino, dimethylamino, diisopropylamino, diethylamino, and the like.

The term "aryl" means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic algal include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 0, 1, 2, or 3 substituents independently selected from alkoxy, alkyl, aryloxy, carboxy, carboxyalkyl, cycloalkyl, cycloalkoxy, halogen, haloalkoxy, haloalkyl, halothioalkoxy, hydroxyl, mercapto, thioalkoxy, thiocycloalkoxy, and thioaryloxy.

The term "aryloxy" means an aryl group, as defined herein, appended to the parent molecular moiety through an oxygen atom. Representative examples of aryloxy include, but are not limited to, phenoxy and tolyloxy.

The term "carbonyl" means a —C(O)— group.

The term "carboxy" means a —CO$_2$H group.

The term "carboxyalkyl" means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cycloalkoxy" means a cycloalkyl group, as defined herein, appended to the parent molecular moiety through an oxygen atom. Representative examples of cycloalkoxy include, but are not limited to, cyclohexyloxy and cyclopropoxy.

The term "cycloalkyl" refers to a monocyclic ring system. Monocyclic ring systems are exemplified by a saturated cyclic hydrocarbon group containing from 3 to 6 carbon atoms. Representative examples of monocyclic ring systems include, but are not limited to, cyclopropyl, cyclobutyl, cyclopentyl, cyclohexyl, and the like.

The term "halo" or "halogen" means —Cl, —Br, —I or —F.

The term "haloalkoxy" means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, difluoromethyl, chloromethyl, 2-fluoroethyl, trifluoromethyl, 2,2,2-trifluoroethyl, pentafluoroethyl, and 2-chloro-3-fluoropentyl.

The term "halothioalkoxy" means at least one halogen, as defined herein, appended to the parent molecular moiety through a thioalkoxy group, as defined herein. Representative examples of halothioalkoxy include, but are not limited to, 2-chloroethylsulfane and trifluoromethylsulfane.

The term "heteroaryl" means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, 1H-pyrrolo[2,3-b]pyridinyl, quinolinyl, quinoxalinyl and thienopyridinyl.

The heteroaryl groups of the invention are optionally substituted with 0, 1, 2, 3 or 4 substituents independently selected from the group consisting of alkoxy, alkyl, aryl, aryloxy, carboxy, carboxyalkyl, cycloalkyl, cycloalkoxy, haloalkoxy, haloalkyl, halogen, halothioalkoxy, thioalkoxy, thiocycloalkoxy, thioaryloxy.

The term "hydroxy" or "hydroxyl" means an —OH group.

The term "mercapto" means a —SH group.

The term "thioalkoxy" refers to an alkyl group, as defined herein, appended to the parent molecular moiety through a sulfur atom. Representative examples of thioalkoxy include, but are not limited to, Representative examples of thioalkoxy include, but are not limited, methylthio, ethylthio, tert-butylthio, and hexylthio.

The term "thiocyloalkoxy" refers to an cycloalkyl group, as defined herein, appended to the parent molecular moiety through a sulfur atom. Representative examples of thiocycloalkoxy include, but are not limited to, cyclopentylsulfane and cyclohexylsulfane.

The term "thiaryloxy" means an aryl group, as defined herein, appended to the parent molecular moiety through a sulfur atom. Representative examples of thioaryloxy include, but are not limited to, thiophenoxy and tolylsulfane.

The term "parenterally" refers to modes of administration, including intravenous, intramuscular, intraperitoneal, intrasternal, subcutaneous, intraarticular injection and infusion.

The term "Positive Allosteric Modulator (PAM)" means a compound that enhances activity of an endogenous ligand, such as but not limited to ACh, or an exogenously administered agonist.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit risk ratio. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid. Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediammonium, ethanolammonium, diethanolammonium, piperidinium, and piperazinium.

The term "pharmaceutically acceptable ester" or "ester" refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I), formula (II), or formula (III) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" or "amide" refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I), formula (II), or formula (III) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the invention in the form of a pharmaceutically acceptable prodrug.

The term "pharmaceutically acceptable prodrug" or "prodrug" represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), formula (II) or formula (III), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" or "carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth malt; gelatin; talc; cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Although typically it may be recognized that an asterisk is used to indicate that the exact subunit composition of a receptor is uncertain, for example α3β4* indicates a receptor that contains the α3 and β4 proteins in combination with other subunits, the term α7 as used herein is intended to include receptors wherein the exact subunit composition is both certain and uncertain. For example, as used herein α7 includes homomeric $(α7)_5$ receptors and α7* receptors, which denote an NNR containing at least one α7 subunit.

COMPOUNDS OF THE INVENTION

One embodiment relates to compounds of formula (I):

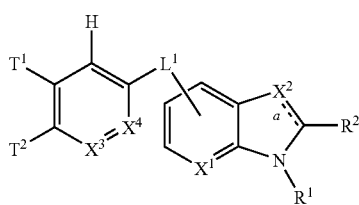

(I)

or a pharmaceutically acceptable salt, ester, amide or prodrug thereof, wherein
$R^1$ is alkylcarbonyl, hydrogen, or methyl;
$R^2$ is hydrogen or methyl;
a is a single or double bond;
$X^1$ is N or CH;
$X^2$ is CH when a is a double bond, and $X^2$ is $CH_2$ or —$CH_2CH_2$— when a is a single bond;
$X^3$ and $X^4$ are independently N or CH;
$T^1$ and $T^2$ are independently hydrogen, alkyl, aryl, cycloalkyl, halo, haloalkyl, or $R^3$-$L^2$-, wherein at least one of $T^1$ and $T^2$ is other than hydrogen;
$L^1$ is —C(O)N(H)$CH_2$— or —N(H)C(O)$CH_2$—;
$L^2$ is O or S; and
$R^3$ is alkyl, aryl, cycloalkyl, or haloalkyl.

Another embodiment relates to compounds of formula (II):

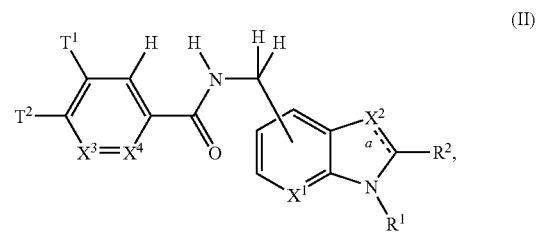

(II)

or a pharmaceutically acceptable salt, ester, amide or prodrug thereof, wherein
$R^1$ and $R^2$ are independently hydrogen or methyl, provided both are not methyl;
a is a single or double bond;
$X^1$ is N or CH;
$X^2$ is CH when a is a double bond, and $X^2$ is CH, or —$CH_2CH_2$— when a is a single bond;
$X^3$ and $X^4$ are independently N or CH;
$T^1$ and $T^2$ are independently hydrogen, aryl, cycloalkyl, halo, haloalkyl, or $R^3$-$L^2$-, wherein at least one of $T^1$ and $T^2$ is other than hydrogen:
$L^2$ is O or S; and
$R^3$ is alkyl, aryl, cycloalkyl, or haloalkyl;
wherein the compound of formula (II) is other than:
3,4-difluoro-N-[(2-methyl-1H-indol-5-yl)methyl]benzamide;
4-bromo-N-[(2-methyl-1H-indol-5-yl)methyl]benzamide;
4-chloro-N-[(2-methyl-1H-indol-5-yl)methyl]benzamide;
3,4-diethoxy-N-[(2-methyl-1H-indol-5-yl)methyl]benzamide;
3,4-dimethoxy-N-[(2-methyl-1H-indol-5-yl)methyl]benzamide;
4-butoxy-N-[(2-methyl-1H-indol-5-yl)methyl]benzamide;
4-isopropoxy-N-[(2-methyl-1H-indol-5-yl)methyl]benzamide;
4-ethoxy-N-[(2-methyl-1H-indol-5-yl)methyl]benzamide;
4-fluoro-N-[(2-methyl-1H-indol-5-yl)methyl]benzamide; or
4-methoxy-N-[(2-methyl-1H-indol-5-yl)methyl]benzamide.

Another embodiment is a compound of formula (II) or a pharmaceutically acceptable salt, ester, amide or prodrug thereof as described above, wherein a is a double bond and $X^2$ is CH.

Another embodiment is a compound of formula (II) or a pharmaceutically acceptable salt, ester, amide or prodrug thereof as described above, wherein a is a single bond and $X^2$ is $CH_2$ or —$CH_2CH_2$—.

Another embodiment is a compound of formula (II) or a pharmaceutically acceptable salt, ester, amide or prodrug thereof as described above, wherein $X^1$ is CH.

Another embodiment is a compound of formula (II) or a pharmaceutically acceptable salt, ester, amide or prodrug thereof as described above, wherein $X^1$ is N.

Another embodiment is a compound of formula (II) or a pharmaceutically acceptable salt, ester, amide or prodrug thereof as described above, wherein $X^3$ and $X^4$ are both CH.

Another embodiment is a compound of formula (II) or a pharmaceutically acceptable salt, ester, amide or prodrug thereof as described above, wherein $X^3$ and $X^4$ are both N.

Another embodiment is a compound of formula (II) or a pharmaceutically acceptable salt, ester, amide or prodrug thereof as described above, wherein one of $X^3$ and $X^4$ is N and the other is CH.

Another embodiment is a compound of formula (II) or a pharmaceutically acceptable salt, ester, amide or prodrug thereof as described above, wherein at least one of $T_1$ and $T^2$ is aryl, cycloalkyl, halo, or haloalkyl.

Another embodiment is a compound of formula (II) or a pharmaceutically acceptable salt, ester, amide or prodrug thereof as described above, wherein at least one of $T^1$ and $T^2$ is $R^3$-$L^2$-, wherein $L^2$ is O or S and $R^3$ is alkyl, haloalkyl or aryl.

Another embodiment is a compound of formula (II) or a pharmaceutically acceptable salt, ester, amide or prodrug thereof as described above, wherein $R^1$ and $R^2$ are both hydrogen, and a is a double bond.

Another embodiment is a compound of formula (II) or a pharmaceutically acceptable salt, ester, amide or prodrug thereof as described above, wherein one of $R^1$ or $R^2$ is hydrogen, the other is methyl, and a is a double bond.

Specific embodiments include, but are not limited to:
6-chloro-N-(1H-indol-5-ylmethyl)nicotinamide;
5-chloro-N-(1H-indol-5-ylmethyl)pyridine-2-carboxamide;
5-bromo-N-(1H-indol-5-ylmethyl)pyridine-2-carboxamide;
N-(1H-indol-5-ylmethyl)-5-(trifluoromethyl)pyridine-2-carboxamide;
N-(1H-indol-5-ylmethyl)-6-(trifluoroethyl)nicotinamide;
N-(1H-indol-5-ylmethyl)-6-(2,2,2-trifluoroethoxy)nicotinamide;
N-(1H-indol-5-ylmethyl)-4-[(trifluoromethyl)thio]benzamide;
4-[(difluoromethyl)thio]-N-(1H-indol-5-ylmethyl)benzamide;
4-[(difluoromethyl)thio]-N-[(1-methyl-1H-indol-5-yl)methyl]benzamide;
N-[(1-methyl-1H-indol-5-yl)methyl]-4-[(trifluoromethyl)thio]benzamide;
N-[(1-methyl-1H-indol-5-yl)methyl]-6-(2,2,2-trifluoroethoxy)nicotinamide;
N-[(1-methyl-1H-indol-6-yl)methyl]-4-[(trifluoromethyl)thio]benzamide;
N-[(1-methyl-1H-indol-4-yl)methyl]-4-[(trifluoromethyl)thio]benzamide;
N-[(2-methyl-1H-indol-5-yl)methyl]-4-[(trifluoromethyl)thio]benzamide;
N-(1H-pyrrolo[2,3-b]pyridin-5-ylmethyl)-6-(2,2,2-trifluoroethoxy)nicotinamide;
4-[(difluoromethyl)thio]-N-(1H-pyrrolo[2,3-b]pyridin-5-ylmethyl)benzamide;
N-(1H-pyrrolo[2,3-b]pyridin-5-ylmethyl)-4-[(trifluoromethyl)thio]benzamide;
N-[(1-methyl-2,3-dihydro-1H-indol-5-yl)methyl]-4-[(trifluoromethyl)thio]benzamide;
N-(2,3-dihydro-1H-indol-5-ylmethyl)-4-[(trifluoromethyl)thio]benzamide;
N-[(1-methyl-1,2,3,4-tetrahydroquinolin-6-yl)methyl]-4-[(trifluoromethyl)thio]benzamide;
N-[(1-methyl-1,2,3,4-tetrahydroquinolin-6-yl)methyl]-6-(2,2,2-trifluoroethoxy)nicotinamide;
N-[(1-acetyl-1H-indol-5-yl)methyl]-6-(2,2,2-trifluoroethoxy)nicotinamide;
N-[(1-acetyl-2,3-dihydro-1H-indol-5-yl)methyl]-4-[(trifluoromethyl)thio]benzamide;
N-(1H-indol-5-ylmethyl)-6-isopropoxynicotinamide;
6-ethoxy-N-(1H-indol-5-ylmethyl)nicotinamide;
N-(1H-indol-5-ylmethyl)-6-methoxynicotinamide;
N-(1H-indol-5-ylmethyl)-6-(trifluoromethoxy)nicotinamide;
N-(1H-indol-5-ylmethyl)-6-propoxynicotinamide;
N-(1H-indol-5-ylmethyl)-6-phenoxynicotinamide;
N-(1H-indol-5-ylmethyl)-6-methoxypyridazin-3-carboxamide;
6-ethoxy-N-(1H-indol-5-ylmethyl)pyridazine-3-carboxamide;
N-(1H-indol-5-ylmethyl)-6-isopropoxypyridazine-3-carboxamide;
N-(1H-indol-5-ylmethyl)-6-propoxypyridazine-3-carboxamide;
N-(1H-indol-5-ylmethyl)-6-(4-methylphenoxy)nicotinamide;
N-(1H-indol-5-ylmethyl)-5-(4-methylphenoxy)pyridine-2-carboxamide;
N-(1H-indol-5-ylmethyl)-4-isopropoxybenzamide;
4-ethoxy-N-(1H-indol-5-ylmethyl)benzamide;
N-(1H-indol-5-ylmethyl)-4-methoxybenzamide;
N-(1H-indol-5-ylmethyl)-4-(trifluoromethoxy)benzamide;
N-(1H-indol-5-ylmethyl)-4-propoxybenzamide;
N-(1H-indol-5-ylmethyl)-4-(2,2,2-trifluoroethoxy)benzamide;
N-(1H-indol-5-ylmethyl)-4-phenoxybenzamide;
N-(1H-indol-5-ylmethyl)-4-(4-methylphenoxy)benzamide;
N-(1H-indol-5-ylmethyl)-5-methoxypyridine-2-carboxamide;
5-ethoxy-N-(1H-indol-5-ylmethyl)pyridine-2-carboxamide;
N-(1H-indol-5-ylmethyl)-5-isopropoxypyridine-2-carboxamide;
N-(1H-indol-5-ylmethyl)-5-propoxypyridine-2-carboxamide;
N-(1H-indol-5-ylmethyl)-5-(trifluoromethoxy)pyridine-2-carboxamide;
N-(1H-indol-5-ylmethyl)-5-(2,2,2-trifluoroethoxy)pyridine-2-carboxamide;
N-(1H-indol-5-ylmethyl)-5-phenoxypyridine-2-carboxamide;
1-(1H-indol-6-ylmethyl)-6-isopropoxynicotinamide;
6-ethoxy-N-(1H-indol-6-ylmethyl)nicotinamide;
N-(1H-indol-6-ylmethyl)-6-methoxynicotinamide;
N-(1H-indol-6-ylmethyl)-6-(trifluoromethoxy)nicotinamide;
N-(1H-indol-6-ylmethyl)-6-propoxynicotinamide;
N-(1H-indol-6-ylmethyl)-6-phenoxynicotinamide;
N-(1H-indol-6-ylmethyl)-6-methoxypyridazin-3-carboxamide;
6-ethoxy-N-(1H-indol-6-ylmethyl)pyridazine-3-carboxamide;
N-(1H-indol-6-ylmethyl)-6-isopropoxypyridazine-3-carboxamide;
N-(1H-indol-6-ylmethyl)-6-propoxypyridazine-3-carboxamide;
N-(1H-indol-6-ylmethyl)-6-(4-methylphenoxy)nicotinamide;
N-(1H-indol-6-ylmethyl)-5-(4-methylphenoxypyridine-2-carboxamide;
N-(1H-indol-6-ylmethyl)-4-isopropoxybenzamide;
4-ethoxy-N-(1H-indol-6-ylmethyl)benzamide;
N-(1H-indol-6-ylmethyl)-4-methoxybenzamide;
N-(1H-indol-6-ylmethyl)-4-(trifluoromethoxy)benzamide;
N-(2,3-dihydro-1H-indol-6-ylmethyl)-4-propoxybenzamide;
N-(1H-indol-6-ylmethyl)-4-(2,2,2-trifluoroethoxy)benzamide;
N-(1H-indol-6-ylmethyl)-4-phenoxybenzamide;
N-(1H-indol-6-ylmethyl)-4-(4-methylphenoxy)benzamide;
N-(1H-indol-6-ylmethyl)-5-methoxypyridine-2-carboxamide;
5-ethoxy-N-(1H-indol-6-ylmethyl)pyridine-2-carboxamide;

N-(1H-indol-6-ylmethyl)-5-isopropoxypyridine-2-carboxamide;
N-(1H-indol-6-ylmethyl)-5-propoxypyridine-2-carboxamide;
N-(1H-indol-6-ylmethyl)-5-(trifluoromethoxy)pyridine-2-carboxamide;
N-(1H-indol-6-ylmethyl)-5-(2,2,2-trifluoroethoxy)pyridine-2-carboxamide;
N-(1H-indol-6-ylmethyl)-5-phenoxypyridine-2-carboxamide;
N-(1H-indol-5-ylmethyl)-6-[(trifluoromethyl)thio]nicotinamide;
N-(1H-indol-5-ylmethyl)-5-[(trifluoromethyl)thio]pyridine-2-carboxamide,
N-(1H-indol-5-ylmethyl)-6-phenylnicotinamide;
N-(1H-indol-5-ylmethyl)-1,1'-biphenyl-4-carboxamide;
N-(1H-indol-5-ylmethyl)-6-phenylpyridazin-3-carboxamide;
N-(1H-indol-5-ylmethyl)-5-phenylpyridine-2-carboxamide;
N-(1H-indol-6-ylmethyl)-6-[(trifluoromethyl)thio]nicotinamide;
N-(1H-indol-6-ylmethyl)-5-[(trifluoromethyl)thio]pyridine-2-carboxamide;
N-(1H-indol-6-ylmethyl)-6-phenylnicotinamide;
N-(1H-indol-6-ylmethyl)-5-phenylpyridine-2-carboxamide;
N-(1H-indol-6-ylmethyl)-6-phenylpyridazin-3-carboxamide;
N-(1H-indol-6-ylmethyl)-1,1'-biphenyl-4-carboxamide;
N-(1H-indol-5-ylmethyl)-4-(trifluoromethyl)benzamide;
N-(1H-indol-5-ylmethyl)-5-(trifluoromethyl)pyridine-2-carboxamide;
N-(1H-indol-5-ylmethyl)-6-(trifluoromethyl)pyridazine-3-carboxamide;
5-chloro-N-(1H-indol-5-ylmethyl)pyridine-2-carboxamide;
4-chloro-N-(1H-indol-5-ylmethyl)benzamide;
4-cyclopropyl-N-(1H-indol-5-ylmethyl)benzamide;
6-cyclopropyl-N-(1H-indol-5-ylmethyl)nicotinamide;
5-cyclopropyl-N-(1H-indol-5-ylmethyl)pyridine-2-carboxamide;
6-cyclopropyl-N-(1H-indol-5-ylmethyl)pyridazine-3-carboxamide;
N-[(2-methyl-1H-indol-5-yl)methyl]-6-(2,2,2-trifluoroethoxy)nicotinamide;
N-(1H-indol-6-ylmethyl)-4-[(trifluoromethyl)thio]benzamide; or
N-(1H-indol-6-ylmethyl)-6-(trifluoromethyl)nicotinamide.

Another embodiment relates to compounds of formula (III):

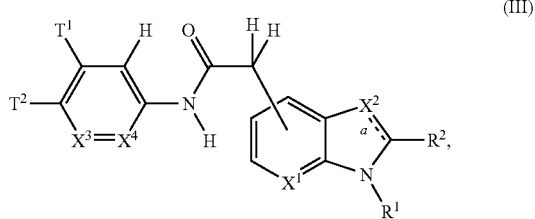

(III)

or a pharmaceutically acceptable salt, ester, amide or prodrug thereof wherein
$R^1$ is alkylcarbonyl, hydrogen, or methyl;
$R^2$ is hydrogen or methyl;
a is a single or double bond;
$X^1$ is N or CH;
$X^2$ is CH when a is a double bond, and $X^2$ is $CH_2$ or $—CH_2CH_2—$ when a is a single bond;
$X^3$ and $X^4$ are independently N or CH;
$T^1$ and $T^2$ are independently hydrogen, alkyl, aryl, cycloalkyl, halo, haloalkyl, or $R^3$-$L^2$-, wherein at least one of $T^1$ and $T^2$ is other than hydrogen;
$L^2$ is O or S; and
$R^3$ is alkyl, aryl, cycloalkyl, or haloalkyl.

Another embodiment is a compound of formula (III) or a pharmaceutically acceptable salt, ester, amide or prodrug thereof as described above, wherein a is a double bond and $X^2$ is CH.

Another embodiment is a compound of formula (III) or a pharmaceutically acceptable salt, ester, amide or prodrug thereof as described above, wherein a is a single bond and $X^2$ is $CH_2$ or $—CH_2CH_2—$.

Another embodiment is a compound of formula (III) or a pharmaceutically acceptable salt, ester, amide or prodrug thereof as described above, wherein $X^1$ is CH.

Another embodiment is a compound of formula (III) or a pharmaceutically acceptable salt, ester, amide or prodrug thereof as described above, wherein $X^1$ is N.

Another embodiment is a compound of formula (III) or a pharmaceutically acceptable salt, ester, amide or prodrug thereof as described above, wherein $X^3$ and $X^4$ are both CH.

Another embodiment is a compound of formula (III) or a pharmaceutically acceptable salt, ester, amide or prodrug thereof as described above, wherein $X^3$ and $X^4$ are both N.

Another embodiment is a compound of formula (III) or a pharmaceutically acceptable salt, ester, amide or prodrug thereof as described above, wherein one of $X^3$ and $X^4$ is N and the other is CH.

Another embodiment is a compound of formula (III) or a pharmaceutically acceptable salt, ester, amide or prodrug thereof as described above, wherein at least one of $T^1$ and $T^2$ is aryl, cycloalkyl, halo, or haloalkyl.

Another embodiment is a compound of formula (III) or a pharmaceutically acceptable salt, ester, amide or prodrug thereof as described above, wherein at least one of $T^1$ and $T^2$ is $R^3$-$L^2$-, wherein $L^2$ is O or S and $R^3$ is alkyl, haloalkyl or aryl.

Another embodiment is a compound of formula (III) or a pharmaceutically acceptable salt, ester, amide or prodrug thereof as described above, wherein $R^1$ and $R^2$ are both hydrogen, and a is a double bond.

Another embodiment is a compound of formula (III) or a pharmaceutically acceptable salt, ester, amide or prodrug thereof as described above, wherein one of $R^1$ or $R^2$ is hydrogen, the other is methyl, and a is a double bond.

Specific embodiments include, but are not limited to:
2-(1H-indol-5-yl)-N-[6-(2,2,2-trifluoroethoxy)pyridin-3-yl]acetamide;
N-{4-[(difluoromethyl)thio]phenyl}-2-(1H-indol-5-yl)acetamide;
2-(1H-indol-5-yl)-N-(4-isopropoxyphenyl)acetamide;
N-(4-ethoxyphenyl)-2-(1H-indol-5-yl)acetamide;
2-(1H-indol-5-yl)-N-(4-methoxyphenyl)acetamide;
2-(1H-indol-5-yl)-N-(4-propoxyphenyl)acetamide;
2-(1H-indol-5-yl)-N-[4-(trifluoromethoxy)phenyl]acetamide;
2-(1H-indol-5-yl)-N-[4-(2,2,2-trifluoroethoxy)phenyl]acetamide;
2-(1H-indol-5-yl)-N-(6-isopropoxypyridine-3-yl)acetamide;
N-(6-ethoxypyridin-3-yl)-2-(1H-indol-5-yl)acetamide;
2-(1H-1-indol-5-yl)-N-(6-methoxypyridin-3-yl)acetamide;
2-(1H-indol-5-yl)-N-(6-propoxypyridin-3-yl)acetamide;

2-(1H-indol-5-yl)-N-[6-(trifluoromethoxy)pyridin-3-yl]acetamide;
2-(1H-indol-5-yl)-N-[6-(2,2,2-trifluoroethoxy)pyridin-3-yl]acetamide;
2-(1H-indol-5-yl)-N-(6-phenoxypyridin-3-yl)acetamide;
2-(1H-indol-5-yl)-N-(6-isopropoxypyridazin-3-yl)acetamide;
N-(6-ethoxypyridazin-3-yl)-2-(1H-indol-5-yl)acetamide;
2-(1H-indol-5-yl)-N-(6-methoxypyridazin-3-yl)acetamide;
2-(1H-indol-5-yl)-N-(6-propoxypyridazin-3-yl)acetamide;
2-(1H-indol-5-yl)-N-[6-(4-methylphenoxy)pyridin-3-yl]acetamide;
2-(1H-indol-5-yl)-N-[5-(4-methylphenoxy)pyridin-2-yl]acetamide;
2-(1H-indol-5-yl)-N-(5-isopropoxypyridine-2-yl)acetamide;
N-(5-ethoxypyridin-2-yl)-2-(1H-indol-5-yl)acetamide;
2-(1H-indol-5-yl)-N-(5-methoxypyridin-2-yl)acetamide;
2-(1H-indol-5-yl)-N-(5-propoxypyridin-2-yl)acetamide;
2-(1H-indol-5-yl)-N-[5-(trifluoromethoxy)pyridin-2-yl]acetamide;
2-(1H-indol-5-yl)-N-[5-(2,2,2-trifluoroethoxy)pyridin-2-yl]acetamide;
2-(1H-indol-5-yl)-N-(5-phenoxypyridin-2-yl)acetamide;
2-(1H-indol-6-yl)-N-(4-isopropoxyphenyl)acetamide;
N-(4-ethoxyphenyl)-2-(1H-indol-6-yl)acetamide;
2-(1H-indol-6-yl)-N-(4-methoxyphenyl)acetamide;
2-(1H-indol-6-yl)-N-(4-propoxyphenyl)acetamide;
2-(1H-indol-6-yl)-N-[4-(trifluoromethoxy)phenyl]acetamide;
2-(1H-indol-6-yl)-N-[4-(2,2,2-trifluoroethoxy)phenyl]acetamide;
2-(1H-indol-6-yl)-N-(6-isopropoxypyridine-3-yl)acetamide;
N-(6-ethoxypyridin-3-yl)-2-(1H-indol-6-yl)acetamide;
2-(1H-indol-6-yl)-N-(6-methoxypyridin-3-yl)acetamide;
2-(1H-indol-6-yl)-N-(6-propoxypyridin-3-yl)acetamide;
2-(1H-indol-6-yl)-N-[6-(trifluoromethoxy)pyridin-3-yl]acetamide;
2-(1H-indol-6-yl)-N-[6-(2,2,2-trifluoroethoxy)pyridin-3-yl]acetamide;
2-(1H-indol-6-yl)-N-(6-phenoxypyridin-3-yl)acetamide;
2-(1H-indol-6-yl)-N-(6-isopropoxypyridazin-3-yl)acetamide;
N-(6-ethoxypyridazin-3-yl)-2-(1H-indol-6-yl)acetamide;
2-(1H-indol-6-yl)-N-(6-methoxypyridazin-3-yl)acetamide;
2-(1H-indol-6-yl)-N-(6-propoxypyridazin-3-yl)acetamide;
2-(1H-indol-6-yl)-N-[6-(4-methylphenoxy)pyridin-3-yl]acetamide;
2-(1H-indol-6-yl)-N-[5-(4-methylphenoxy)pyridin-2-yl]acetamide;
2-(1H-indol-6-yl)-N-(5-isopropoxypyridine-2-yl)acetamide;
N-(5-ethoxypyridin-2-yl)-2-(1H-indol-6-yl)acetamide;
2-(1H-indol-6-yl)-N-(5-methoxypyridin-2-yl)acetamide;
2-(1H-indol-6-yl)-N-(5-propoxypyridin-2-yl)acetamide;
2-(1H-indol-6-yl)-N-[5-(trifluoromethoxy)pyridin-2-yl]acetamide;
2-(1H-indol-6-yl)-N-[5-(2,2,2-trifluoroethoxy)pyridin-2-yl]acetamide;
2-(1H-indol-6-yl)-N-(5-phenoxypyridin-2-yl)acetamide;
N-(1H-indol-5-ylmethyl)-5-[(trifluoromethyl)thio]pyridine-2-carboxamide;
2-(1H-indol-5-yl)-N-{6-[(trifluoromethyl)thio]pyridin-3-yl}acetamide;
2-(1H-indol-5-yl)-N-{5-[(trifluoromethyl)thio]pyridin-2-yl}acetamide;
2-(1H-indol-5-yl)-N-{6-[(trifluoromethyl)thio]pyridazin-3-yl}acetamide;
2-(1H-indol-5-yl)-N-(6-phenylpyridin-3-yl)acetamide;
2-(1H-indol-5-yl)-N-(5-phenylpyridin-2-yl)acetamide;
N-1,1-biphenyl-4-yl-2-(1H-indol-5-yl)acetamide;
2-(1H-indol-5-yl)-N-(6-phenylpyridazin-3-yl)acetamide;
2-(1H-indol-6-yl)-N-{6-[(trifluoromethyl)thio]pyridin-3-yl}acetamide;
2-(1H-indol-6-yl)-N-{5-[(trifluoromethyl)thio]pyridin-2-yl}acetamide;
2-(1H-indol-6-yl)-N-{6-[(trifluoromethyl)thio]pyridazin-3-yl}acetamide;
2-(1H-indol-6-yl)-N-(6-phenylpyridin-3-yl)acetamide;
2-(1H-indol-6-yl)-N-(5-phenylpyridin-2-yl)acetamide;
2-(1H-indol-6-yl)-N-(6-phenylpyridazin-3-yl)acetamide;
N-1,1'-biphenyl-4-yl-2-(1H-indol-6-yl)acetamide;
2-(1H-indol-5-yl)-N-[4-(trifluoromethyl)phenyl]acetamide;
2-(1H-indol-5-yl)-N-[5-(trifluoromethyl)pyridin-2-yl]acetamide;
2-(1H-indol-5-yl)-N-[6-(trifluoromethyl)pyridazin-3-yl]acetamide;
N-(4-cyclopropylphenyl)-2-(1H-indol-5-yl)acetamide;
N-(6-cyclopropylpyridin-3-yl)-2-(1H-indol-5-yl)acetamide;
N-(5-cyclopropylpyridin-2-yl)-2-(1H-indol-5-yl)acetamide;
N-(6-cyclopropylpyridazin-3-yl)-2-(1H-indol-5-yl)acetamide;
N-[4-(3-chlorophenoxy)phenyl]-2-(1H-indol-5-yl)acetamide;
N-[4-(2,5-dichlorophenoxy)phenyl]-2-(1H-indol-5-yl)acetamide;
2-(1H-indol-5-yl)-N-{4-[4-(trifluoromethoxy)phenoxy]phenyl}acetamide;
N-[4-(4-chlorophenoxy)phenyl]-2-(1H-indol-5-yl)acetamide;
N-[6-(3-chlorophenoxy)pyridin-3-yl]-2-(1H-indol-5-yl)acetamide;
N-[6-(2,5-dichlorophenoxy)pyridin-3-yl]-2-(1H-indol-5-yl)acetamide;
2-(1H-indol-5-yl)-N-{6-[4-(trifluoromethoxy)phenoxy]pyridin-3-yl}acetamide;
N-[6-(4-chlorophenoxy)pyridin-3-yl]-2-(1H-indol-5-yl)acetamide;
N-[5-(3-chlorophenoxy)pyridin-2-yl]-2-(1H-indol-5-yl)acetamide;
N-[5-(2,5-dichlorophenoxy)pyridin-2-yl]-2-(1H-indol-5-yl)acetamide;
2-(1H-indol-5-yl)-N-{5-[4-(trifluoromethoxy)phenoxy]pyridin-2-yl}acetamide;
N-[5-(4-chlorophenoxy)pyridin-2-yl]-2-(1H-indol-5-yl)acetamide;
2-(1H-indol-5-yl)-N-[6-(phenylthio)pyridin-3-yl]acetamide;
N-{6-[(2,5-dichlorophenyl)thio]pyridin-3-yl}-2-(1H-indol-5-yl)acetamide;
2-(1H-indol-5-yl)-N-(6-{[3-(trifluoromethoxy)phenyl]thio}pyridin-3-yl)acetamide;
2-(2-methyl-1H-indol-5-yl)-N-[6-(2,2,2-trifluoroethoxy)pyridin-3-yl]acetamide;
2-(1H-indol-5-yl)-N-{4-[(trifluoromethyl)thio]phenyl}acetamide;
N-{4-[(difluoromethyl)thio]phenyl}-2-(1H-indol-5-yl)acetamide;
2-(1H-indol-5-yl)-N-[6-(2,2,2-trifluoroethoxy)pyridin-3-yl]acetamide;
2-(1H-indol-5-yl)-N-[6-(trifluoromethyl)pyridin-3-yl]acetamide;
2-(1H-indol-5-yl)-N-(4-phenoxyphenyl)acetamide;

2-(1H-indol-5-yl)-N-{3-[(trifluoromethyl)thio]phenyl}acetamide; or

N-(6-chloropyridin-3-yl)-2-(1H-indol-5-yl)acetamide.

Compounds may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds including geometric isomers of carbon-carbon double bonds and carbon-nitrogen double bonds are included in the present invention. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds described herein are encompassed within the scope of the present invention.

Amides, Esters and Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", pp. 97-118, which is incorporated in its entirety by reference herein.

Esters can be prepared from substrates of formula (I), formula (II), or formula (III) containing either a hydroxyl group or a carboxy group by general methods known to persons skilled in the art. The typical reactions of these compounds are substitutions replacing one of the heteroatoms by another atom, for example:

Scheme 1

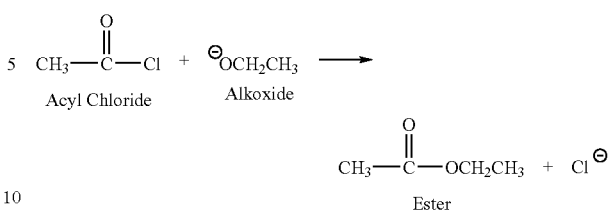

Amides can be prepared from substrates of formula (I), formula (II), or formula (III) containing either an amino group or a carboxy group in similar fashion. Esters can also react with amines or ammonia to form amides.

Scheme 2

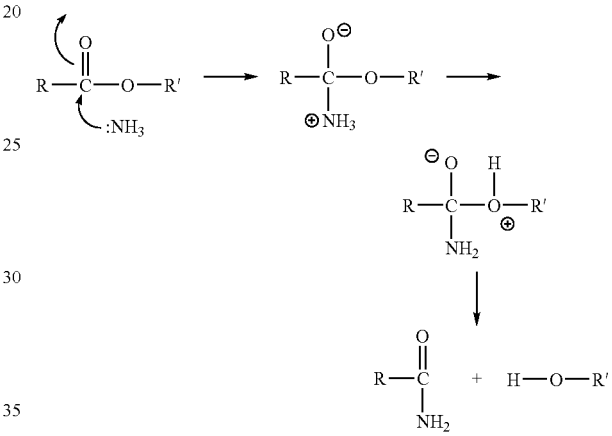

Another way to make amides from compounds of formula (I), formula (II), or formula (III) is to heat carboxylic acids and amines together.

Scheme 3

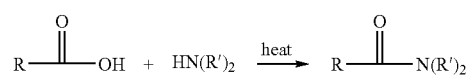

In Schemes 2 and 3, R and R' are independently substrates of formula (I), formula (II), formula (III), alkyl or hydrogen. Various embodiments of formula (I), formula (II), or formula (III) that are substrates for prodrugs, amides and esters include, but not limited to, Examples 1, 2, 3, 4, 5, 6, 7, 8, 14, 15, 16, 17, 19, 22, 23 and Examples 26-197. Examples 24 and 25 are representative prodrugs of the invention.

COMPOSITIONS OF THE INVENTION

The invention also provides pharmaceutical compositions comprising a therapeutically effective amount of a compound of formula (I), formula (II), or formula (III) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the knows art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds and compositions of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq. Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds and compositions of the invention can be used in the form of pharmaceutically acceptable salts, esters, or amides derived from inorganic or organic acids. The pharmaceutically acceptable salts, esters and amides include salts, zwitterions, esters and amides of compounds of formula (I), formula (II), or formula (III) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Yet another aspect of the invention relates to radiolabelled or isotopically labelled pharmaceutical compositions. Radiolabelled or isotopically labelled forms of compounds of formula (I), formula (II), or formula (III) are provided as compositions of the invention and administered in accordance with the method of the invention. The radiolabelled or isotopically labelled forms of compounds of formula (I), formula (II), or formula (III) may be used as a pharmaceutical agent or may be useful in the discovery of other compounds which are modulators of α7 NNR. In these uses, the compounds of the invention possess at least one atom of a deuterium or tritium.

METHODS OF THE INVENTION

Compounds and compositions of the invention are useful for modulating the effects of NNRs, particularly by allosteric modulation. Such compounds can be useful for the treatment and prevention of a number of NNR-mediated diseases or conditions.

A population of α7 NNRs in the spinal cord modulate serotonergic transmission that has been associated with the pain-relieving effects of nicotinic compounds (Cordero-Erausquin, M., et al., *Proc. Nat. Acad. Sci.* 2001, 98: 2803-2807). The α7 NNR ligands demonstrate therapeutic potential for the treatment of pain states, including acute pain, post-surgical pain, as well as chronic pain states including inflammatory pain and neuropathic pain. Moreover, α7 NNRs are expressed on the surface of primary macrophages that are involved in the inflammation response, and that activation of the α7 NNR inhibits release of tumor necrosis factor (TNF) and other cytokines that trigger the inflammation response (Wang, H., *Nature,* 2003, 421: 384-388). TNF-α plays a pathological role in diverse inflammatory diseases including arthritis and psoriasis and endometriosis. Therefore, selective α7 NNR ligands and modulators demonstrate potential for treating conditions involving inflammation and pain.

α7 NNRs have been shown to play a significant role in enhancing cognitive function, including aspects of learning, memory and attention (Levin, E. D., *J. Neurobiol.,* 2002, 53: 633-640). As such, α7 ligands are suitable for the treatment of cognitive disorders including, for example, attention deficit disorder, ADHD, AD, MCI, senile dementia, AIDS dementia, Pick's Disease, dementia associated with Lewy bodies, and dementia associated with Down's syndrome, as well as cognitive deficits associated with schizophrenia.

In addition, α7 NNRs have been shown to be involved in the neuroprotective effects of nicotine both in vitro (Jonnala, R. B. et al., *J. Neurosci. Res.,* 2001, 66: 565-572) and in vivo (Shimohama, S., *Brain Res.,* 1998, 779: 359-363). More particularly, neurodegeneration underlies several progressive CNS disorders, including, but not limited to, AD, Parkinson's disease, amyotrophic lateral sclerosis, Huntington's disease, dementia with Lewy bodies, as well as diminished CNS function resulting from traumatic brain injury. For example, the impaired function of α7 NNRs by β-amyloid peptides linked to AD has been implicated as a key factor in development of the cognitive deficits associated with the disease (Liu, Q.-S., et al., *PNAS,* 2001, 98: 4734-4739). The activation of α7 NNRs has been shown to block this neurotoxicity (Kihara, T., *J. Biol. Chem.,* 2001, 276: 13541-13546). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 NNRs in this disease, including a measured deficit of these receptors in post-mortem patients (Leonard, S., *Eur. J. Pharmacol.,* 2000, 393: 237-242). Deficits in sensory processing (gating) are one of the hallmarks of schizophrenia. These deficits can be normalized by nicotinic ligands that operate at the α7 NNR (Adler, L. E. *Schizophrenia Bull.,* 1998, 24: 189-202; Stevens, K. E., *Psychopharmacology,* 1998, 136: 320-327). Thus, α7 NNR ligands demonstrate potential in the treatment of schizophrenia.

Compounds of the invention are particularly useful for treating and preventing a condition or disorder affecting cognition, neurodegeneration, and schizophrenia. Cognitive impairment associated with schizophrenia often limits the ability of patients to function normally; a symptom not adequately treated by commonly available treatments, for example, treatment with an atypical antipsychotic (Rowley, M., *J. Med. Chem.*, 2001, 44: 477-501). Such cognitive deficit has been linked to dysfunction of the nicotinic cholinergic system, in particular with decreased activity at α7 NNR receptors (Friedman, J. I., *Biol. Psychiatry,* 2002, 51: 349-357). Thus, activators of α7 NNR receptors can provide useful treatment for enhancing cognitive function in schizophrenic patients who are being treated with atypical antipsychotics. Accordingly, the combination of an α7 NNR modulator and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like. Accordingly, it is contemplated that compounds of formula (I), formula (II), or formula (III) of the invention also can be administered in combination with an atypical antipsychotic.

One of the measurable abnormalities in schizophrenic patients, is the P50 auditory gating deficit, an indication of impaired information processing and diminished ability to "filter" unimportant or repetitive sensory information. On the basis of clinical observations that these deficits are normalized by nicotine, it has been suggested that the high prevalence of smoking among patients with schizophrenia (>80%) may be a form of self medication. Pharmacological studies have shown that nicotine's mechanisms of action is via α7 NNRs. Restoration of P50 gating deficits in humans by α7 selective ligands, agonists and PAMs could lead to discontinuation of continuous smoking. Therefore, NNR ligands that are selective for the α7 subtype and can be used in therapy for smoking cessation, with an improved side effect profile compared to nicotine.

Accordingly, the administration of a therapeutically effective amount of a compound of formula (I), formula (II), or formula (III) to a mammal provides a method of treating or preventing condition or disorder selected from attention deficit disorder, ADHD, AD, MCI, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, depression, pain, acute pain, post-surgical pain, chronic pain, inflammation, inflammatory pain, neuropathic pain, osteoarthritic pain, chronic lower back pain, migraine, and smoking cessation.

Accordingly, an embodiment is directed to a method of treating conditions and disorders that are regulated by the NNRs using compounds of formula (I), formula (II), or formula (III) or therapeutically effective compositions of compounds of formula (I), formula (II), or formula (III).

Another embodiment relates to a method of using compounds of formula (I), formula (II), or formula (III), or a pharmaceutically acceptable salt, ester, amide or prodrug thereof. Compositions containing compounds of formula (I), formula (II), or formula (III) can be administered in accordance with described methods, typically as part of a therapeutic regimen for treatment or prevention of conditions and disorders related to NNR activity, and more particularly allosteric modulation of NNR activity.

Another embodiment is a method of using compounds of formula (I), formula (II), or formula (III) for treating or preventing conditions and disorders related to NNR modulation in mammals. More particularly, the method is useful for conditions and disorders related to attention deficit disorder, ADHD, AD, MCI, schizophrenia, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, depression, pain, acute pain, post-surgical pain, chronic pain, inflammation, inflammatory pain, neuropathic pain, osteoarthritic pain, chronic lower back pain, migraine, smoking cessation, and various other conditions modulated by α7 NNRs modulators.

Another embodiment is a method of using compounds of formula (I), formula (II), or formula (III) for treating or preventing conditions and disorders related to NNR modulation in mammals, wherein the conditions and disorders are attention deficit disorder, ADHD, AD, MCI, schizophrenia, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury and depression.

Another embodiment is a method of using compounds of formula (I), formula (II), or formula (III) for treating or preventing conditions and disorders related to NNR modulation in mammals, wherein the conditions and disorders are pain, acute paint post-surgical pain, chronic pain, inflammation, inflammatory pain, neuropathic pain, osteoarthritic pain, chronic lower back pain, migraine, and smoking cessation.

Another embodiment relates to a method of using compounds of formula (I), formula (II), or formula (III) for treating or preventing conditions and disorders related to NNR modulation in mammals. More particularly, the method is useful for combining a compound of formula (I), formula (II), or formula (III) with an atypical antipsychotic. Further, in another embodiment, the invention is a method of administering the compositions containing compounds of formula (I), formula (II), or formula (III) in combination with a nicotinic agonist or an atypical antipsychotic.

Another embodiment relates to a method of using compositions or compounds of formula (I), formula (II), or formula (III), or a pharmaceutically acceptable salt, ester, amide or prodrug thereof, in combination with a cholinesterase inhibitor or another drug that increases endogenous acetylcholine release such as histamine H3 antagonists, 5HT-6 antagonists, dopamine D3 agonists, muscarinic receptor antagonists and potassium channel blockers, leading to potentiation of effects at the α7 nicotinic receptor subtype.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal ranges from about 0.001 mg/kg body weight to about 1 g/kg body weight. More preferable doses can be in the range of from about 0.001 mg/kg body weight to about 100 mg/kg body weight. If desired, the effective daily dose can be divided into multiple doses for purposes of administration. Consequently, single dose compositions may contain such amounts or submultiples thereof to make up the daily dose.

Another embodiment relates to a method of assessing or diagnosing conditions or disorders related to α7 NNR activity comprising allowing isotope-labeled forms of compounds of formula (I), formula (II), or formula (III) to interact with cells expressing endogenous α7 NNRs or cells expressing recombinant α7 NNRs and measuring the effects of such isotope-labeled forms of compounds on such cells as explained in Determination of Biological Activity section.

Another embodiment relates to methods of using NNR PAM compounds to identify other useful target compounds for treating or preventing, or both, diseases or conditions associated with NNR function, in cell-based assays, for example in high-throughput format, using cells or tissues that express native α7 NNRs for the purpose of identifying novel α7 NNR agonists or PAMs of α7 NNRs.

Another embodiment is a method of identifying an α7 NNR agonist comprising allowing a compound of formula (I), formula (II), or formula (III) to interact with cells or cell lines endogenously expressing α7 NNRs or cells expressing recombinant α7 NNRs in a fluorescent medium and measuring changes in such fluorescence by known protocols or as described in Determination of Biological Activity section.

Preparation of Compounds of Formula (I), Formula (II) or Formula (III)

The methods described below can entail use of various enantiomers. The compounds of this invention can be prepared according to the synthetic methods described in this section, Methods of the Invention and Examples sections. Certain groups described in the Schemes are meant to illustrate certain substituents contained within the invention and are not intended to limit the scope of the invention. Representative procedures are shown in, but are not limited to, Schemes 4-11.

Scheme 4

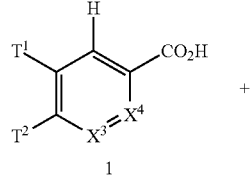

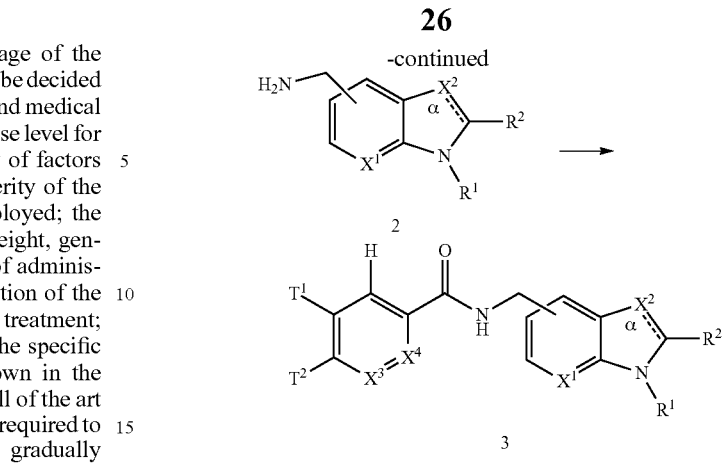

As outlined in Scheme 4, compounds of formula 3 are representative of compounds of formula (I), formula (II), or formula (III) wherein $R^1$, $R^2$, $T^1$, $T^2$, $X^1$, $X^2$, $X^3$, $X^4$, and a are as defined in formula (I), formula (II), or formula (III), can be prepared accordingly. Compounds of formula 1 when treated with compounds of formula 2 in a solvent such as dimethylformamide in the presence of a base such as N,N-diisopropylethylamine and a coupling reagent such as O-(7-azabenzotriazol-1-yl)-N,N',N'-tetramethyluronium hexafluorophosphate at or near room temperature for a period of 6 to 24 hours furnishes compounds of formula 3.

Alternative conditions and reagents to form compounds of formula 3 include combining an equimolar mixture of the compounds of formula 1 and compounds of formula 2 with a coupling reagent such as but not limited to bis(2-oxo-3-oxazolidinyl)phosphinic chloride (BOPCI), 1,3-dicyclohexyl-carbodiimide (DCC), polymer supported 1,3-dicyclohexyl-carbodiimide (PS-DCC), O-(7-azabenzotriazol-1-yl)-N,N,N',N'-tetramethyluronium hexafluorophosphate (HAATU), O-benzotriazol-1-yl-N,N,N',N'-tetramethyluronium tetrafluoroborate (TBTU) optionally along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine, and triethylamine in solvents such as, but not limited to, tetrahydrofuran, N,N-dimethylacetamide, N,N-dimethylformamide, pyridine and chloroform. Typical reactions can be carried out between 0-65° C. or may be carried out in a microwave reactor to facilitate the coupling.

Scheme 5

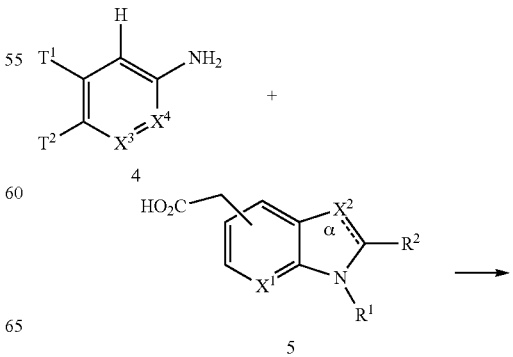

27

-continued

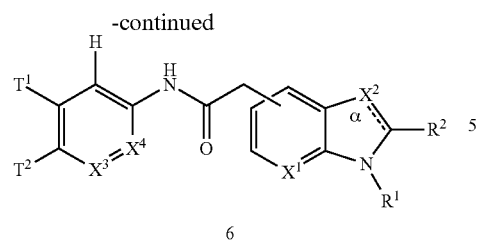

6

28

-continued

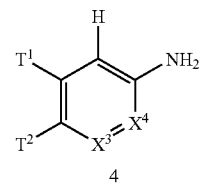

4

As outlined in Scheme 5, compounds of formula 6 are representative of compounds of formula (I), formula (II), or formula (III), wherein $R^1$, $R^2$, $T^1$, $T^2$, $X^1$, $X^2$, $X^3$, $X^4$, and a are as defined in formula (I), formula (II), or formula (III), can be prepared accordingly. Compounds of formula 6 can be prepared by combining an equimolar mixture of the compounds of formula 4 and compounds of formula 5 with a coupling reagent such as but not limited to bis(2-oxo-3-oxazolidinyl) phosphinic chloride (BOPCl), 1,3-dicyclohexyl carbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU) optionally along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine, and triethylamine in solvents such as, but not limited to, tetrahydrofuran, N,N-dimethylacetamide, N,N-dimethylformamide, pyridine and chloroform. Typical reactions can be carried out between 0-65° C. or may be carried out in a microwave reactor to facilitate the coupling.

As outlined in Scheme 6, compounds of formula 4, wherein $T^1$, $T^2$, $X^3$, and $X^4$ are as defined in formula (I), formula (II), or formula (III), can be prepared from compounds of formula 1 by a sequence involving a Curtius rearrangement. Methods for effecting this transformation include treatment with diphenylphosphoryl azide in a solvent such as toluene or an alcohol, with trapping of the intermediate isocyanate by water, methanol, benzyl alcohol, or allyl alcohol. The carbamate 7, wherein R" is hydrogen, methyl, benzyl or allyl, can be converted to aniline 4 under conditions appropriate for each R" (e.g., iodotrimethylsilane for methyl ($CH_3$), $H_2$/catalyst for benzyl ($CH_2Ph$), Pd°/nucleophile for allyl ($CH_2CH=CH_2$). Compounds of formula 4 can be used as described in Scheme 5.

Scheme 6

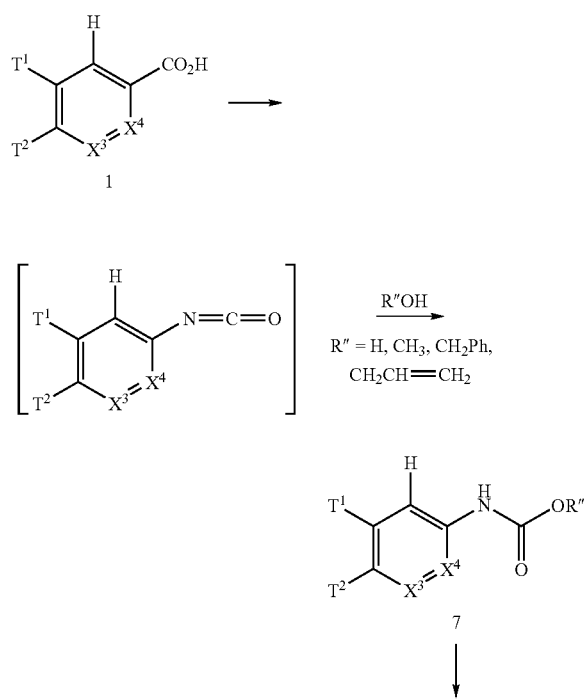

Scheme 7

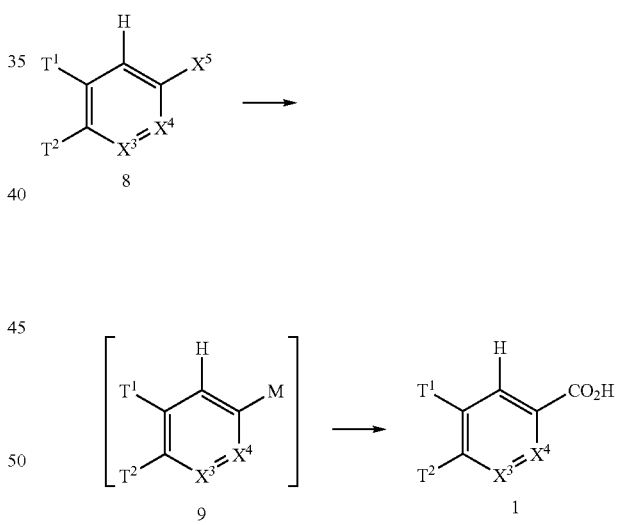

As outlined in Scheme 6, carboxylic acids of formula 1, wherein $T^1$, $T^2$, $X^3$, and $X^4$ are as defined in formula (I), formula (II), or formula (III) and M is lithium or magnesium, can be prepared from compounds of formula 8, wherein $X^5$ is Cl, Br, I, or trifluoromethylsulfonate, by halogen-metal exchange with lithium, n-butyllithium, magnesium, or other metals, followed by quenching with carbon dioxide. Alternately, 8 can be treated with palladium and methyl chloroformate. Compounds of formula 1 can be used as described in Scheme 4.

Scheme 8

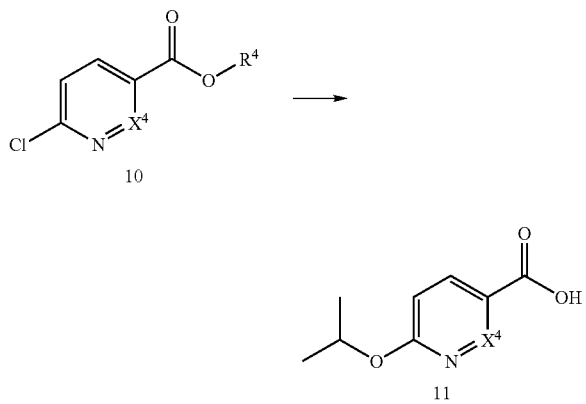

As described in Scheme 8, compounds of formula 11, wherein $X^4$ is as defined in formula (I), formula (II), or formula (III), can be prepared from compounds of formula 10, wherein $R^4$ is methyl, ethyl, or benzyl, and sodium isopropoxide in a solvent such as 2-propanol, followed by ester hydrolysis using either an aqueous acid such as hydrochloric acid or a base such as sodium hydroxide, potassium hydroxide, or lithium hydroxide in water or a mixture of water and a cosolvent such as tetrahydrofuran (Konno, S.; et al., *Heterocycles* 1992, 34, 225-8). Compounds or formula 11 can be used in place of compounds of formula 1 in Scheme 4.

Scheme 9

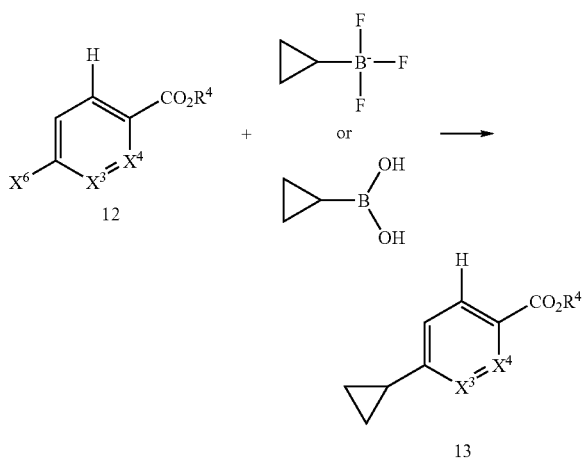

As described in Scheme 9, compounds of formula 13, wherein $X^3$ and $X^4$ are as defined in formula (I), formula (II), or formula (III), can be prepared from compounds of formula 12, wherein $X^6$ is bromine, iodine, or chlorine and $R^4$ is methyl, ethyl, or benzyl, by reacting with either cyclopropylboronic acid or potassium cyclopropyl trifluoroborate under cross-coupling reaction conditions according to the following literature descriptions: Wallace, D. J.; et al., *Tetrahedron Lett.* 2002, 43, 6987-6990; Fang, G.-H.; Yan, Z.-J.; et al., *Org. Lett.* 2004, 6, 357-360; or Charette. A. B.; et al., *Synlett* 2005, 1779-1782. The esters of formula 13 can be hydrolyzed to the corresponding carboxylic acids using methodologies known to one skilled in the art which can then be used in place of compounds of formula 1 in Scheme 4.

Scheme 10

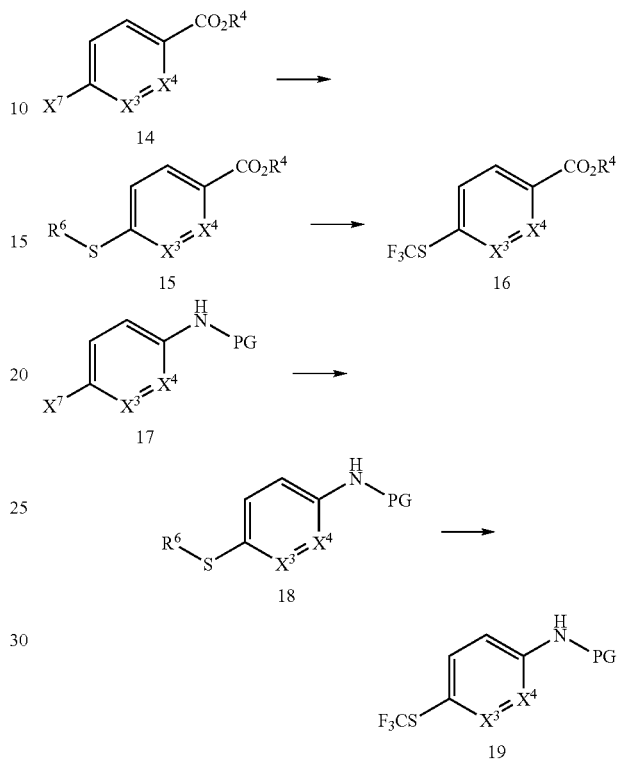

As described in Scheme 10, compounds of formula 16 or formula 19, wherein $X^3$ and $X^4$ are as defined for formula (I), formula (II), or formula (III), $R^4$ is methyl, ethyl, or benzyl, and PG represents a nitrogen protecting group as described below, can be prepared from compounds of formula 15 and formula 18, respectively, wherein $R^6$ is H or $SR^5$ ($SR^5$ is indicative of a symmetric disulfide) by treatment with trimethylsilyl trifluoromethane and a catalytic amount of an activator such as tetrabutylammonium fluoride (Prakash, G. K. S.; et al., *Chem. Rev.* 1997, 97, 757-786).

Alternatively, conversion to the trifluoromethylsulfide can be effected by treatment with at least 4.2 equivalents of iodotrifluoromethane and 2.2 equivalents of tetrakis(dimethylamino)ethylene (TDAE) in N,N-dimethylformamide at 0° C. to room temperature (Carreño, M. C.; et al., *Org. Lett.* 2004, 6, 297-299).

Compounds of formula 15 and formula 18 can be prepared from compounds of formula 14 and formula 17 ($X^7$=F, Cl, Br. I, trifluoromethylsulfonate), respectively, by displacement with thiourea, sodium thiolate, or sodium thioacetate.

The ester of compounds of formula 16 and protecting groups of compounds of formula 19 can be removed with methodologies known to one skilled in the art. The corresponding carboxylic acids of compounds of formula 16 can be used in place of compounds of formula 1 in Scheme 4. The corresponding anilines of compounds of formula 19 can be used in place of compounds of formula 4 in Scheme 5.

Scheme 11

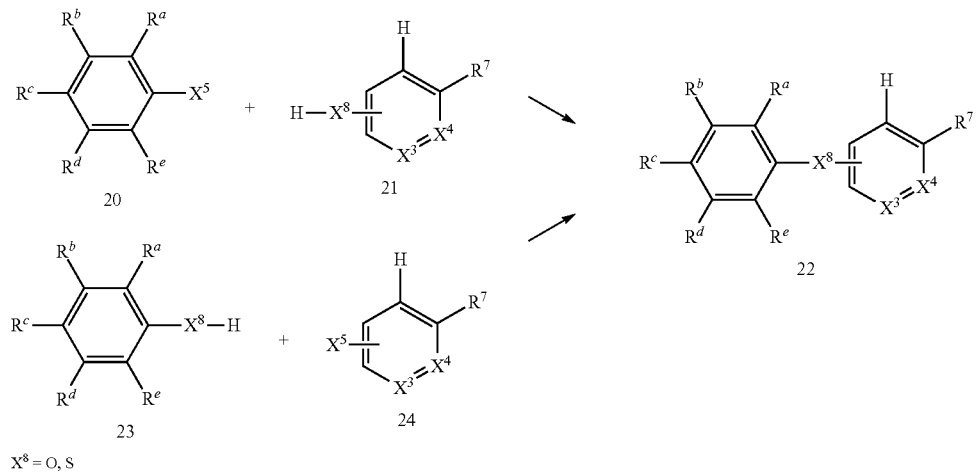

$X^8 = O, S$

As described in Scheme 11, compounds of formula 22, wherein $X^3$ and $X^4$ are as defined for formula (I), formula (II), or formula (III), $X^7$ is oxygen or sulfur, and $R^a$, $R^b$, $R^c$, $R^d$ and $R^e$ are hydrogen or aryl (phenyl) substituents described in the Definition of Terms, can be prepared from compounds of formula 20 and formula 21 or formula 23 and formula 24. $R^7$ represents either an ester (—$CO_2R^4$) or a protected aniline (—NHPG) as described in Scheme 10 and $X^5$ is Cl, Br, I, or trifluoromethylsulfonate. The phenols or thiophenols of formula 21 and formula 23 can be coupled under Ullmann reaction conditions with the corresponding aryl halides or aryl triflates of formula 20 and formula 24, respectively. Copper-mediated Ullmann reaction conditions to prepare diaryl ethers or diaryl thioethers have been described in the following literature citation: Ley, S. V.; et al. *Angew. Chem. Int. Ed.* 2003, 42, 5400-5449. Compounds of formula 22 upon conversion to the corresponding carboxylic acids or anilines can be used in Schemes 4 and 5, respectively.

In addition, nitrogen protecting groups can be used for protecting amine groups during the synthesis of compounds of formula (I), formula (II), or formula (III). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium, potassium or lithium hydroxide in aqueous organic or alcoholic solvents.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Some compounds of the invention have at least one basic site whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic acid, atrolactic acid, methanesulfonic acid, ethanesulfonic acid, toluenesulfonic acid, naphthalenesulfonic acid, carbonic acid, fumaric acid, gluconic acid, acetic acid, propionic acid, salicylic acid, hydrochloric acid, hydrobromic acid, phosphoric acid, sulfuric acid, citric acid, or hydroxybutyric acid, camphorsulfonic acid, malic acid, phenylacetic acid, aspartic acid, glutamic acid, and the like.

The invention contemplates pharmaceutically active compounds either chemically synthesized or formed by in vivo biotransformation to compounds of formula (I), formula (II), or formula (III).

The compounds, compositions, and methods of the invention will be better understood by reference to the following examples and reference examples, which are intended as an illustration of and not a limitation upon the scope of the invention.

EXAMPLES

Abbreviations

DMSO for dimethyl sulfoxide, HPLC for high-pressure liquid chromatography, PA for polymer supported, FBS for fetal bovine serum, HBSS for Hank's Balanced Salt Solution, HEPES for 4-(2-hydroxyethyl)-1-piperazineethanesulfonic acid, PBS for phosphate buffered saline, SDS for sodium dodecyl sulfate, Tween for polyoxyethylenesorbitan monolaurate, and HBC for (2-hydroxypropyl)-β-cyclodextrin.

General Procedure for Amide Formation (Method A):

A suspension of an amine component (0.5 mmol) and a carboxylic acid component (0.5 mmol) in anhydrous dimethylformamide (2 mL) was treated with N,N-diisopropylethylamine (iPr₂NEt; 245 µL, 1.5 mmol, 3.0 equivalents; Acros) and O-(7-azabenzotriazol-1-yl)-N,N,N',N'-tetramethyluronium hexafluorophosphate (HATU; 285 mg, 0.75 mmol, 1.5 equivalents; Aldrich). The mixture was stirred overnight at room temperature and then diluted with dichloromethane (20 mL). The solution was washed with dilute aqueous ammonium chloride (2×7 mL), dilute aqueous sodium bicarbonate (2×7 ml), and brine (2×7 mL). The organic layer was dried over sodium sulfate, filtered, and concentrated in vacuo. The resulting material was purified by either flash chromatography [Analogix pre-packed silica gel cartridges, 5-50% gradient of ethyl acetate/hexanes], or by preparative HPLC [Waters Xterra RP₁₈ 30×100 mm column, flow rate 40 mL/min. 5-95% gradient of acetonitrile in buffer (0.1 M aqueous ammonium bicarbonate, adjusted to pH 10 with sodium hydroxide)] to afford the desired amide product as its free base. Alternatively, the compound was purified on a Waters Symmetry® C₈ 30×100 mm column (flow rate 40 mL/min. 5-95% gradient of acetonitrile in 0.1% aqueous trifluoroacetic acid) to afford the amide product after evaporation of solvent.

Example 1

6-chloro-N-(1H-indol-5-ylmethyl)nicotinamide

The titled compound was prepared from 6-chloronicotinic acid (Aldrich) and (1H-indol-5-yl)methylamine (Aldrich) according to method A: $^1$H NMR (300 MHz, CDCl₃) δ ppm 4.73 (d, J=5.42 Hz, 2H) 6.31 (br s, 1H) 6.55 (s, 1H) 7.14-7.26 (m, 2H) 7.40 (d, J=8.14 Hz, 2H) 7.64 (s, 1H) 8.09 (dd, J=8.31, 2.54 Hz, 1H) 8.22 (br s, 1H) 8.74 (d, J=2.71 Hz, 1H); MS (DCI/NH₃) m/z 286.1 (M+H)⁺.

Example 2

5-chloro-N-(1H-indol-5-ylmethyl)pyridine-2-carboxamide

The titled compound was prepared from 5-chloropyridine-2-carboxylic acid (Matrix) and (1H-indol-5-yl)methylamine (Aldrich) according to method A: $^1$H NMR (300 MHz. CDCl₃) δ ppm 4.74 (d, J=5.76 Hz, 2H) 6.53 (d, 1H) 7.16-7.24 (m, 2H) 7.38 (d, J=8.48 Hz, 1H) 7.64 (s, 1H) 7.82 (dd, J=8.48, 2.37 Hz, 1H) 8.20 (d, J=9.15 Hz, 1H) 8.44 (d, J=2.37 Hz, 1H); MS (DCI/NH₃) m/z 286.1 (M+H)⁺, 303 (M+NH₄)⁺.

Example 3

5-bromo-N-(1H-indol-5-ylmethyl)pyridine-2-carboxamide

The titled compound was prepared from 5-bromo-2-pyridinecarboxylic acid (Matrix) and (1H-indol-5-yl)methylamine (Aldrich) according to method A: $^1$H NMR (300 MHz, CDCl₃) δ ppm 4.74 (d, J=5.76 Hz, 2H) 6.54 (s, 1H) 7.15-7.24 (m, 2H) 7.38 (d, J=8.48 Hz, 1H) 7.64 (s, 1H) 7.91-8.04 (m, 1H) 8.08-8.26 (br s, 1H) 8.14 (d, J=8.48 Hz, 1H) 8.55 (d, J=3.05 Hz, 1H); MS (DCI/NH₃) m/z 330.0 (M+H)⁺, 347.1 (M+NH₄)⁺.

Example 4

N-(1H-indol-5-ylmethyl)-5-(trifluoromethyl)pyridine-2-carboxamide

The titled compound was prepared from 5-(trifluoromethyl)pyridine-2-carboxylic acid (Matrix) and (1H-indol-5-yl)methylamine (Aldrich) according to method A: $^1$H NMR (300 MHz, CDCl₃) δ ppm 4.77 (d, J=6.10 Hz, 2H) 6.54 (s, 1H) 7.18-7.25 (m, 2H) 7.39 (d, J=9.16 Hz, 1H) 7.65 (s, 1H) 8.09 (d, J=2.71 Hz, 1H) 8.18 (br s, 1H) 8.29 (br s, 1H) 8.39 (d, J=8.82 Hz, 1H) 8.77 (s, 1H); MS (DCI/NH₃) m/z 320.1 (M+H)⁺.

Example 5

N-(1H-indol-5-ylmethyl)-6-(trifluoromethyl)nicotinamide

The titled compound was prepared from 6-(trifluoromethyl)nicotinic acid (Apollo) and (1H-indol-5-yl)methylamine (Aldrich) according to method A: $^1$H NMR (300 MHz, CDCl₃) δ ppm 4.77 (d, J=5.42 Hz, 2H) 6.39 (br s, 1H) 6.49-6.64 (m, 1H) 7.16-7.24 (m, 2H) 7.41 (d, J=8.48 Hz, 1H) 7.65 (s, 1H) 7.76 (d, J=7.46 Hz, 1H) 8.22 (br s, 1H) 8.31 (dd, J=8.14, 2.37 Hz, 1H) 9.06 (s, 1H); MS (DCI/NH₃) m/z 320.0 (M+H)⁺, 337.1 (M+NH₄)⁺.

Example 6

N-(1H-indol-5-ylmethyl)-6-(2,2,2-trifluoroethoxy)nicotinamide

The titled compound was prepared from 6-(2,2,2-trifluoroethoxy)nicotinic acid (Matrix) aid (1H-indol-5-yl)methylamine (Aldrich) according to method A: $^1$H NMR (300 MHz, CDCl₃) δ ppm 4.73 (d. J=5.09 Hz, 2H) 4.79 (q. J=8.48 Hz, 2H) 6.24 (br s, 1H) 6.49-6.60 (m, 1H) 6.90 (d. J=8.48 Hz, 1H) 7.14-7.25 (m, 2H) 7.40 (d, J=8.14 Hz, 1H) 7.63 (s, 1H) 8.07 (d, J=11.19 Hz, 1H) 8.21 (br s, 1H) 8.56 (d, J=2.71 Hz, 1H); MS (DCI/NH₃) m/z 340.1 (M+H)⁺, 357.1 (M+NH₄)⁺; Anal. Calc'd: C, 58.45; H, 4.04; N, 12.03. Found C, 58.16; H, 3.87; N, 11.91.

Example 7

N-(1H-indol-5-ylmethyl)-4-[(trifluoromethyl)thio]benzamide

The titled compound was prepared from 4-(trifluoromethyl-thio)benzoic acid (Aldrich) and (1H-indol-5-yl)methylamine (Aldrich) according to method A: $^1$H NMR (300 MHz, CDCl₃) δ ppm 4.74 (d, J=5.43 Hz, 2H) 6.32 (br s, 1H) 6.51-6.58 (m, 1H) 7.16-7.24 (m, 2H) 7.40 (d, J=8.48 Hz, 1H) 7.63 (s, 1H) 7.67-7.74 (m, 2H) 7.78-7.87 (m, 2H) 8.19 (br s, 1H); MS (DCI/NH₃) m/z 351.1 (M+H)⁺, 368.1 (M+NH₄)⁺; Anal. Calc'd: C, 58.28; H, 3.74; N, 8.00. Found C, 58.14; H, 3.72; N, 7.94.

Example 8

4-[(difluoromethyl)thio]-N-(1H-indol-5-ylmethyl)benzamide

A sealed tube was charged with sodium 2-chloro-2,2-difluoroacetate (0.525 g, 3.44 mmol) and sodium bicarbonate (0.284 g, 3.38 mmol) in dimethylformamide (14 mL). The vessel was purged with nitrogen, and 4-mercaptobenzoic acid (0.35 g, 2.270 mmol) was added. The mixture was warmed to 80° C. for 3 hours. The reaction mixture was then cooled and filtered to remove a precipitate. The dimethylformamide was diluted with diethyl ether (200 mL) and dichloromethane (75 mL) and acidified to pH 4.8 with acetic acid (0.5 mL). The resulting cloudy solution was extracted with a dilute solution of aqueous sodium chloride (3×150 mL) followed by brine (2×150 mL).

The organic layer was concentrated onto silica for loading onto a column. The product was collected after filtration through silica (40 g column, 1:1 ethyl acetate/hexane eluent). The crude product, 4-(difluoromethylthio)benzoic acid (0.273 g) was used as such in the next step: $^1$H NMR (300

MHz, methanol-d$_4$) δ ppm 7.21 (t, J=56.3 Hz, 1H) 7.62-7.70 (AA'BB', 2H) 8.00-8.08 (AA'BB', 2H); MS (ESI–) m/z 202.8 (M–H)⁻.

The titled product was prepared from 4-(difluoromethylthio)benzoic acid and (1H-indol-5-yl)methylamine (Aldrich) according to method A: $^1$H NMR (300 MHz, CDCl$_3$) δ ppm 4.73 (d, J=5.43 Hz, 2H) 6.24-6.39 (br s, 1H) 6.55 (s, 1H) 6.85 (t, J=56.29 Hz, 1H) 7.17-7.25 (m, 3H) 7.40 (d, J=8.14 Hz, 1H) 7.57-7.67 (m, 2H) 7.79 (d, J=8.14 Hz, 2H) 8.13-8.27 (br s, 1H); MS (DCI/NH$_3$) m/z 333.1 (M+H)⁺, 350.1 (M+NH$_4$)⁺; Anal. Calc'd: C, 61.43; H, 4.25; N, 8.43. Found C, 61.22; H, 3.91; N, 8.31.

Example 9

4-[(difluoromethyl)thio]-N-[(1-methyl-1H-indol-5-yl)methyl]benzamide

The titled compound was prepared from 4-(difluoromethylthio)benzoic acid (prepared as described in example 8) and (1-methyl-1H-indol-5-yl)methanamine (Maybridge) according to method A: $^1$H NMR (300 MHz, CDCl$_3$) δ ppm 3.81 (s, 3H) 4.65-4.80 (m, 2H) 6.31 (br s, Hz, 1H) 6.47 (d, J=4.07 Hz, 1H) 6.85 (t, J=56.62 Hz, 1H) 7.08 (d, J=3.05 Hz, 1H) 7.18-7.25 (m, 1H) 7.29-7.35 (m, 1H) 7.57-7.65 (m, 3H) 7.79 (d, J=8.81 Hz, 2H); MS (DCI/NH$_3$) m/z 347.1 (M+H)⁺, 364.2 (M+NH$_4$)⁺; Anal. Calc'd: C, 62.41; H, 4.66; N, 8.09. Found C, 62.00; H, 4.46; N, 8.01.

Example 10

N-[(1-methyl-1H-indol-5-yl)methyl]-4-[(trifluoromethyl)thio]benzamide

The titled compound was prepared from 4-(trifluoromethylthio)benzoic acid (Aldrich) and (1-methyl-1H-indol-5-yl)methanamine (Maybridge) according to method A: $^1$H NMR (300 MHz, methanol-d$_4$) δ ppm 3.78 (s, 3H) 4.66 (s, 2H) 6.38 (s, 1H) 7.13 (d, J=3.05 Hz, 1H) 7.19 (dd, J=8.48, 1.70 Hz, 1H) 7.34 (d, J=8.48 Hz, 1H) 7.54 (s, 1H) 7.77 (d, J=8.48 Hz, 2H) 7.93 (d, J=8.48 Hz, 2H); MS (DCI/NH$_3$) m/z 365.1 (M+H)⁺, 392.1 (M+NH$_4$)⁺; Anal. Calc'd: C, 59.33; H, 4.15; N, 7.69. Found C, 59.15; H, 4.07; N, 7.61.

Example 11

N-[(1-methyl-1H-indol-5-yl)methyl]-6-(2,2,2-trifluoroethoxy)nicotinamide

The titled compound was prepared from 6-(2,2,2-trifluoroethoxy)nicotinic acid (Maybridge) and (1-methyl-1H-indol-5-yl)methanamine (Maybridge) according to method A: $^1$H NMR (300 MHz, CDCl$_3$) δ ppm 3.81 (s, 3H) 4.67-4.76 (m, 2H) 4.75-4.88 (m, 2H) 6.23 (br s, 1H) 6.47 (d, J=3.05 Hz, 1H) 6.89 (d, J=8.48 Hz, 1H) 7.08 (d, J=3.05 Hz, 1H) 7.17-7.24 (m, 1H) 7.28-7.36 (m, 1H) 7.61 (s, 1H) 8.07 (d, J=11.19 Hz, 1H) 8.55 (s, 1H); MS (DCI/NH$_3$) m/z 364.1 (M+H)⁺, 391.4 (M+NH$_4$)⁺; Anal. Calc'd: C, 59.50; H, 4.44; N, 11.57. Found C, 59.76; H, 4.16; N, 11.37.

Example 12

N-[(1-methyl-1H-indol-6-yl)methyl]-4-[(trifluoromethyl)thio]benzamide

In a 96 deep well plate, 4-(trifluoromethylthio)benzoic acid (23 mg, 0.10 mmol) was added dissolved in dimethylacetamide (0.4 mL), followed by O-(7-azabenzotriazol-1-yl)-N,N,N',N'-tetramethyluronium hexafluorophosphate (HATU, 48 mg, 0.12 mmol, 1.2 equivalents) dissolved in dimethylacetamide (0.3 mL), triethylamine (26 mg, 0.25 mmol, 2.4 equivalents) dissolved in dimethylacetamide (0.3 mL), and finally the N-(1-methyl-1H-indol-6-yl)methanamine (0.7 mL of a 0.2 M solution in dimethylacetamide, 1.4 equivalents). This was shaken at room temperature overnight. The reaction solution was concentrated to dryness in vacuo, dissolved in 1:1 dimethyl sulfoxide/methanol and purified by reverse phase HPLC (Phenomenex® Luna® C8(2) 5 umn 100 Å AXIA™ column (30 mm×75 mm), a gradient of acetonitrile (A) and 0.1% trifluoroacetic acid in water (B) was used, at a flow rate of 40 mL/min (0-0.5 min 10% A, 0.5-6.0 min linear gradient 10-100% A, 6.0-7.0 min 100% A, 7.0-8.0 min linear gradient 100-10% A)) to give the titled product: $^1$H NMR (500 MHz, DMSO-d$_6$/D$_2$O) δ ppm 3.76 (s, 3H) 4.61 (s, 2H) 6.40 (dd, J=3.1, 0.6 Hz, 1H) 7.05 (dd, J=8.1, 1.4 Hz, 1H) 7.28 (d, J=3.1 Hz, 1H) 7.39 (s, 1H) 7.51 (d, J=7.9 Hz, 1H) 7.81-7.85 (m, 2H) 7.97-8.01 (m, 2H), 9.22 (s, 1H); MS (ESI+) m/z 365.0 (M+H)⁺.

Example 13

N-[(1-methyl-1H-indol-4-yl)methyl]-4-[(trifluoromethyl)thio]benzamide

The titled compound was prepared from 4-(trifluoromethylthio)benzoic acid and N-(1-methyl-1H-indol-4-yl)methanamine as described for example 12. The titled product was obtained following HPLC purification: $^1$H NMR (500 MHz, DMSO-d$_6$/D$_2$O) δ ppm 3.78 (s, 3H) 4.75 (d, J=5.5 Hz, 2H) 6.57 (dd, J=3.1, 0.6 Hz, 1H) 6.99 (d, J=7.0 Hz, 1H) 7.12 (dd, J=8.0, 7.0 Hz, 1H) 7.31 (d, J=3.1 Hz, 1H) 7.36 (d, J=8.2 Hz, 1H) 7.12 (d, J=8.2 Hz, 2H) 7.96-8.00 (m, 2H) 9.22 (t, J=5.8 Hz, 1H); MS (ESI+) m/z 365.0 (M+H)⁺.

Example 14

N-[(2-methyl-1H-indol-5-yl)methyl]-4-[(trifluoromethyl)thio]benzamide

The titled compound was prepared from 4-(trifluoromethylthio)benzoic acid and N-(2-methyl-1H-indol-5-yl)methanamine as described for example 12. The titled product was obtained following HPLC purification: $^1$H NMR (500 MHz, DMSO-d$_6$/D$_2$O) δ ppm 2.36 (s, 3H) 4.53 (s, 2H) 6.08 (s, 1H) 7.00 (dd, J=8.2, 1.5 Hz, 1H) 7.23 (d, J=8.2 Hz, 1H) 7.35 (s, 1H) 7.80-7.84 (m, 2H) 7.96-8.01 (m, 2H), 9.20 (s, 1H); MS (ESI–) m/z 363.1 (M–H)⁻.

Example 15

N-(1H-pyrrolo[2,3-b]pyridin-5-ylmethyl)-6-(2,2,2-trifluoroethoxy)nicotinamide

The titled compound was prepared from 6-(2,2,2-trifluoroethoxy)nicotinic acid (Maybridge) and N-(1H-pyrrolo[2,3-b]pyridin-5-ylmethyl)methanamine (Maybridge) according to method A: $^1$H NMR (300 MHz, methanol-d$_4$) δ ppm 4.74 (s, 2H) 4.88-5.00 (m, 2H) 6.75 (d, J=3.57 Hz, 1H) 6.93-7.03 (m, 1H) 7.61 (d, J=3.57 Hz, 1H) 8.19 (dd, J=8.72, 2.38 Hz, 1H) 8.39 (s, 1H) 8.49 (s, 1H) 8.69 (d, J=2.38 Hz, 1H); MS (DCI/NH$_3$) m/z 364.1 (M+H)⁺, 351.1; Anal. Calc'd: C, 46.56; H, 3.04; N, 12.07. Found C, 46.88; H, 2.89; N, 12.63.

Example 16

4-[(difluoromethyl)thio]-N-(1H-pyrrolo[2,3-b]pyridin-5-ylmethyl)benzamide

The titled compound was prepared from 4-(difluoromethylthio)benzoic acid prepared as described in Example 8 and N-(1H-pyrrolo[2,3-b]pyridin-5-ylmethyl)methanamine (ADESIS) according to method A: $^1$H NMR (300 MHz, CDCl₃) δ ppm 4.79 (d, J=5.55 Hz, 2H) 6.54 (d, J=3.57 Hz, 1H) 6.63-7.07 (m, 2H) 7.43-7.51 (m, 2H) 7.62 (d. J=8.33 Hz, 2H) 7.85 (d. J=4.76 Hz, 2H) 8.02 (s, 1H); MS (DCI/NH₃) m/z 334.0 (M+H)⁺.

Example 17

N-(1H-pyrrolo[2,3-b]pyridin-5-ylmethyl)-4-[(trifluoromethyl)thio]benzamide

The titled compound was prepared from 4-(trifluoromethylthio)benzoic acid (Aldrich) and N-(1H-pyrrolo[2,3-b]pyridin-5-ylmethyl)methanamine (ADESIS) according to method A: ¹H NMR (300 MHz, CDCl₃) δ ppm 4.77 (d, J=5.55 Hz, 2H) 6.39 (br s, 1H) 6.46-6.55 (m, 1H) 7.31-7.38 (m, 1H) 7.66-7.77 (m, 2H) 7.77-7.87 (m, 2H) 7.98 (s, 1H) 8.32 (s, 1H) 8.73 (br s, 1H); MS (DCI/NH₃) m/z 352.1 (M+H)⁺.

Example 18

N-[(1-methyl-2,3-dihydro-1H-indol-5-yl)methyl]-4-[(trifluoromethyl)thio]benzamide N-(1H-indol-5-ylmethyl)-4-[(trifluoromethyl)thio]benzamide (Example 7, 98.7 mg, 0.280 mmol) and formaldehyde (4.0 mL, 53.7 mmol) were dissolved in methanol (4.0 mL). The resulting solution was cooled to 0° C. in an ice bath. Sodium triacetoxyborohydride was added in portions to the chilled solution. After 30 minutes, the ice bath was removed and the reaction mixture was stirred at room temperature for 2 hours. The reaction mixture was made basic by addition of 4 N sodium hydroxide. Volatiles were removed under reduced pressure. The residue was partitioned between water and dichloromethane. The organic layer was dried over magnesium sulfate, filtered and concentrated. The residue was purified by flash chromatography (12 g SiO₂ column, gradient 5-60% ethyl acetate in hexanes) to give the titled compound: ¹H NMR (300 MHz, CDCl₃) δ ppm 2.76 (s, 3H) 2.94 (t, J=8.31 Hz, 2H) 3.32 (t, J=8.14 Hz, 2H) 4.52 (d, J=5.42 Hz, 2H) 6.22 (br s, 1H) 6.44 (d, J=7.80 Hz, 1H) 7.01-7.12 (m, 2H) 7.65-7.74 (m, 2H) 7.76-7.85 (m, 2H); MS (DCI/NH₃) m/z 367.1 (M+H)⁺, 384.1 (M+NH₄)⁺; Anal. Calc'd: C, 56.54; H, 4.48; N, 7.33. Found C, 56.54; H, 4.65; N, 7.63.

Example 19

N-(2,3-dihydro-1H-indol-5-ylmethyl)-4-[(trifluoromethyl)thio]benzamide

N-(1H-indol-5-ylmethyl)-4-[(trifluoromethyl)thio]benzamide (Example 7, 117 mg, 0.335 mmol) was dissolved in acetic acid (1 mL) and methanol (1 mL). Sodium cyanoborohydride (63 mg, 1.00 mmol) was added in one portion. The reaction mixture was stirred under dry nitrogen overnight. The reaction mixture was made basic by addition of 4 N sodium hydroxide. Volatiles were removed under reduced pressure. The residue was partitioned between water and dichloromethane. The organic layer was dried over magnesium sulfate, filtered and concentrated. The residue was purified by flash chromatography (12 g SiO₂ column, gradient 5-60% ethyl acetate in hexanes) to give the titled compound: ¹H NMR (300 MHz, CDCl₃) δ ppm 3.04 (t, J=8.31 Hz, 2H) 3.59 (t, J=8.48 Hz, 2H) 4.53 (d. J=5.42 Hz, 2H) 6.65 (d, J=7.80 Hz, 1H) 7.01 (d, J=6.78 Hz, 1H) 7.13 (s, 1H) 7.66-7.77 (m, 2H) 7.77-7.87 (m, 2H); MS (DCI/NH₃) m/z 353.1 (M+H)⁺, 370.1 (M+NH₄)⁺.

Example 20

N-[(1-methyl-1,2,3,4-tetrahydroquinolin-6-yl)methyl]-4-[(trifluoromethyl)thio]benzamide The titled compound was prepared from 4-(trifluoromethylthio)benzoic acid (Aldrich) and (1-methyl-1,2,3,4-tetrahydroquinolin-6-yl)methanamine (Chembridge) according to method A: ¹H NMR (300 MHz, CDCl₃) δ ppm 1.84-2.09 (m, 2H) 2.76 (t, J=6.54 Hz, 2H) 2.89 (s, 3H) 3.12-3.33 (m, 2H) 4.49 (d, J=5.55 Hz, 2H) 6.20 (br s, 1H) 6.56 (d, J=8.33 Hz, 1H) 6.95 (d, J=1.98 Hz, 1H) 7.05 (d, J=8.33 Hz, 1H) 7.65-7.74 (m, 2H) 7.75-7.86 (m, 2H); MS (DCI/NH₃) m/z 334.0 (M+H)⁺, 351.1 (M+NH₄)⁺; Anal. Calc'd: C, 59.99; H, 5.03; N, 7.36. Found C, 60.34; H, 4.87; N, 7.17.

Example 21

N-[(1-methyl-1,2,3,4-tetrahydroquinolin-6-yl)methyl]-6-(2,2,2-trifluoroethoxy)nicotinamide The titled compound was prepared from 6-(2,2,2-trifluoroethoxy)nicotinic acid (Maybridge) and (1-methyl-1,2,3,4-tetrahydroquinolin-6-yl)methanamine (Chembridge) according to method A: ¹H NMR (300 MHz, CDCl₃) δ ppm 1.88-2.10 (m, 2H) 2.76 (t, J=6.35 Hz, 2H) 2.89 (s, 3H) 3.15-3.29 (m, 2H) 4.39-4.56 (m, 2H) 4.69-4.88 (m, 2H) 6.11 (br s, 1H) 6.57 (d, J=8.33 Hz, 1H) 6.89 (d, J=8.72 Hz, 1H) 6.95 (s, 1H) 7.05 (d, J=8.33 Hz, 1H) 8.06 (d, J=11.10 Hz, 1H) 8.54 (s, 1H); MS (DCI/NH₃) m/z 380.1 (M–H)⁺, 397.2 (M+NH₄)⁺; Anal. Calc'd: C, 60.15; H, 5.31; N, 11.08. Found C, 59.38; H, 5.00; N, 10.81.

Example 22

2-(1H-indol-5-yl)-N-[6-(2,2,2-trifluoroethoxy)pyridin-3-yl]acetamide

The titled compound is prepared according to method A from 4-(2,2,2-trifluoroethoxy)aniline (Maybridge) and 1H-indol-5-ylacetic acid (Naruto, S.; Yonemitsu, O. *Chem. Pharm. Bull.* (1972), 20 (10) p. 2163-2171).

Example 23

N-{4-[(difluoromethyl)thio]phenyl}-2-(1H-indol-5-yl)acetamide

The titled compound is prepared from 4-(difluoromethylthio)aniline and 1H-indol-5-ylacetic acid according to method A.

Example 24

N-[(1-acetyl-1H-indol-5-yl)methyl]-6-(2,2,2-trifluoroethoxy)nicotinamide

The titled compound is prepared from Example 6 and acetyl chloride using the procedure described in Illi, V. O. *Synthesis* 1979, 387-388.

Example 25

N-[(1-acetyl-2,3-dihydro-1H-indol-5-yl)methyl]-4-[(trifluoromethyl)thio]benzamide The titled compound is prepared from Example 19 and acetic anhydride using the procedure described in Bolton., R. E.; et al., *J. Chem. Soc., Chem. Commun.* 1985, 1775-1776.

Examples 26-190 listed below are prepared as described in the Examples, Schemes, or by procedures well known to one skilled in the art. The starting materials are either available from commercial sources or are prepared as described in the Examples, Schemes, or by procedures well known to one skilled in the art:

Example 26

N-(1H-indol-5-ylmethyl)-6-isopropoxynicotinamide;

Example 27

6-ethoxy-N-(1H-indol-5-ylmethyl)nicotinamide;

Example 28

N-(1H-indol-5-ylmethyl)-6-methoxynicotinamide;

Example 29

N-(1H-indol-5-ylmethyl)-6-(trifluoromethoxy)nicotinamide;

Example 30

N-(1H-indol-5-ylmethyl)-6-propoxynicotiniamide;

Example 31

N-(1H-indol-5-ylmethyl)-6-phenoxynicotinamide;

Example 32

N-(1H-indol-5-ylmethyl)-6-methoxypyridazin-3-carboxamide;

Example 33

6-ethoxy-N-(1H-indol-5-ylmethyl)pyridazine-3-carboxamide;

Example 34

N-(1H-indol-5-ylmethyl)-6-isopropoxypyridazine-3-carboxamide;

Example 35

N-(1H-indol-5-ylmethyl)-6-propoxypyridazine-3-carboxamide;

Example 36

N-(1H-indol-5-ylmethyl)-6-(4-methylphenoxy)nicotinamide;

Example 37

N-(1H-indol-5-ylmethyl)-5-(4-methylphenoxy)pyridine-2-carboxamide;

Example 38

N-(1H-indol-5-ylmethyl)-4-isopropoxybenzamide;

Example 39

4-ethoxy-N-(1H-indol-5-ylmethyl)benzamide;

Example 40

(N-(1H-indol-5-ylmethyl)-4-methoxybenzamide;

Example 41

N-(1H-indol-5-ylmethyl)-4-(trifluoromethoxy)benzamide;

Example 42

N-(1H-indol-5-ylmethyl)-4-propoxybenzamide;

Example 43

N-(1H-indol-5-ylmethyl)-4-(2,2,2-trifluoroethoxy)benzamide;

Example 44

N-(1H-indol-5-ylmethyl)-4-phenoxybenzamide;

Example 45

2-(1H-indol-5-yl)-N-(4-isopropoxyphenyl)acetamide;

Example 46

N-(4-ethoxyphenyl)-2-(1H-indol-5-yl)acetamide;

Example 47

2-(1H-indol-5-yl)-N-(4-methoxyphenyl)acetamide;

Example 48

2-(1H-indol-5-yl)-N-(4-propoxyphenyl)acetamide;

Example 49

2-(1H-indol-5-yl)-N-[4-(trifluoromethoxy)phenyl]acetamide;

Example 50

2-(1H-indol-5-yl)-N-[4-(2,2,2-trifluoroethoxy)phenyl]acetamide;

Example 51

N-(1H-indol-5-ylmethyl)-4-(4-methylphenoxy)benzamide;

Example 52

2-(1H-indol-5-yl)-N-(6-isopropoxypyridine-3-yl)acetamide;

Example 53

N-(6-ethoxypyridin-3-yl)-2-(1H-indol-5-yl)acetamide;

Example 54

2-(1H-indol-5-yl)-N-(6-methoxypyridin-3-yl)acetamide;

Example 55

2-(1H-indol-5-yl)-N-(6-propoxypyridin-3-yl)acetamide;

Example 56

2-(H-indol-5-yl)-N-[6-(trifluoromethoxy)pyridin-3-yl]acetamide;

Example 57

2-(1H-indol-5-yl)-N-[6-(2,2,2-trifluoroethoxy pyridin-3-yl]acetamide;

Example 58

2-(1H-indol-5-yl)-N-(6-phenoxypyridin-3-yl)acetamide;

Example 59

2-(1H-indol-5-yl)-N-(6-isopropoxypyridazin-3-yl)acetamide;

Example 60

N-(6-ethoxypyridazin-3-yl)-2-(1H-indol-5-yl)acetamide;

Example 61

2-(1H-indol-5-yl)-N-(6-methoxypyridazin-3-yl)acetamide;

Example 62

2-(1H-indol-5-yl)-N-(6-propoxypyridazin-3-yl)acetamide

Example 63

2-(1H-indol-5-yl)-N-[6-(4-methylphenoxy)pyridin-3-yl]acetamide;

Example 64

2-(1H-indol-5-yl)-N-[5-(4-methylphenoxy)pyridin-2-yl]acetamide;

Example 65

N-indol-5-ylmethyl)-5-methoxypyridine-2-carboxamide;

Example 66

5-ethoxy-N-(1H-indol-5-ylmethyl)pyridine-2-carboxamide;

Example 67

N-(1H-indol-5-ylmethyl)-5-isopropoxypyridine-2-carboxamide;

Example 68

N-(1H-indol-5-ylmethyl)-5-propoxypyridine-2-carboxamide;

Example 69

N-(1H-indol-5-ylmethyl)-5-(trifluoromethoxy)pyridine-2-carboxamide;

Example 70

N-(1H-indol-5-ylmethyl)-5-(2,2,2-trifluoroethoxy)pyridine-2-carboxamide;

Example 71

N-(1-indol-5-ylmethyl)-5-phenoxypyridine-2-carboxamide;

Example 72

2-(1H-indol-5-yl)-N-(5-isopropoxypyridine-2-yl)acetamide;

Example 73

N-(5-ethoxypyridin-2-yl)-2-(1H-indol-5-yl)acetamide;

Example 74

2-(1H-indol-5-yl)-N-(5-methoxypyridin-2-yl)acetamide;

Example 75

2-(1H-indol-5-yl)-N-(5-propoxypyridin-2-yl)acetamide;

Example 76

2-(1H-indol-5-yl)-1-[S-(trifluoromethoxy)pyridin-2-yl]acetamide;

Example 77

2-(1H-indol-5-yl)-N-[5-(2,2,2-trifluoroethoxy)pyridin-2-yl]acetamide;

Example 78

2-(1H-indol-5-yl)-N-(5-phenoxypyridin-2-yl)acetamide;

Example 79

N-(1H-indol-6-ylmethyl)-6-isopropoxynicotinamide;

Example 80

6-ethoxy-N-(1H-indol-6-ylmethyl)nicotinamide;

Example 81

N-(1H-indol-6-ylmethyl)-6-methoxynicotinamide;

Example 82

N-(1H-indol-6-ylmethyl)-6-(trifluoromethoxy)nicotinamide;

Example 83

N-(1H-indol-6-ylmethyl)-6-propoxynicotinamide;

Example 84

N-(1H-indol-6-ylmethyl)-6-phenoxynicotinamide;

Example 85

N-(1H-indol-6-ylmethyl)-6-methoxypyridazin-3-carboxamide;

Example 86

6-ethoxy-N-(1H-indol-6-ylmethyl)pyridazine-3-carboxamide;

Example 87

N-(1H-indol-6-ylmethyl)-6-isopropoxypyridazine-3-carboxamide;

Example 88

N-(1H-indol-6-ylmethyl)-6-propoxypyridazine-3-carboxamide;

Example 89

N-(1H-indol-6-ylmethyl)-6-(4-methylphenoxy)nicotinamide;

Example 90

N-(1H-indol-6-ylmethyl)-5-(4-methylphenoxy)pyridine-2-carboxamide;

Example 91

N-(1-indol-6-ylmethyl)-4-isopropoxybenzamide;

Example 92

4-ethoxy-N-(1H-indol-6-ylmethyl)benzamide;

Example 93

N-(1H-indol-6-ylmethyl)-4-methoxybenzamide;

Example 94

N-(1H-indol-6-ylmethyl)-4-(trifluoromethoxy)benzamide;

Example 95

N-(2,3-dihydro-1H-indol-6-ylmethyl)-4-propoxybenzamide;

Example 96

N-(1H-indol-6-ylmethyl)-4-(2,2,2-trifluoroethoxy)benzamide;

Example 97

N-(1H-indol-6-ylmethyl)-4-phenoxybenzamide;

Example 98

2-(1H-indol-6-yl)-N-(4-isopropoxyphenyl)acetamide;

Example 99

N-(4-ethoxyphenyl)-2-(1H-indol-6-yl)acetamide;

Example 100

2-(1H-indol-6-yl)-N-(4-methoxyphenyl)acetamide;

Example 101

2-(1H-indol-6-yl)-N-(4-propoxyphenyl)acetamide;

Example 102

2-(1H-indol-6-yl)-N-[4-(trifluoromethoxy)phenyl]acetamide;

Example 103

2-(1H-indol-6-yl)-N-[4-(2,2,2-trifluoroethoxy)phenyl]acetamide;

Example 104

N-(1H-indol-6-ylmethyl)-4-(4-methylphenoxy)benzamide;

Example 105

2-(1H-indol-6-yl)-N-(6-isopropoxypyridine-3-yl)acetamide;

Example 106

N-(6-ethoxypyridin-3-yl)-2-(1H-indol-6-yl)acetamide;

Example 107

2-(1H-indol-6-yl)-N-(6-methoxypyridin-3-yl)acetamide;

Example 108

2-(1H-indol-6-yl)-N-(6-propoxypyridin-3-yl)acetamide;

Example 109

2-(1H-indol-6-yl)-N-[6-(trifluoromethoxy)pyridin-3-yl]acetamide;

Example 110

2-(1H-indol-6-yl)-N-[6-(2,2,2-trifluoroethoxy)pyridin-3-yl]acetamide,

Example 111

2-(1H-indol-6-yl)-N-(6-phenoxypyridin-3-yl)acetamide;

Example 112

2-(1H-indol-6-yl)-AN-(6-isopropoxypyridazin-3-yl)acetamide;

Example 113

N-(6-ethoxypyridazin-3-yl)-2-(1H-indol-6-yl)acetamide;

Example 114

2-(1H-indol-6-yl)-N-(6-methoxypyridazin-3-yl)acetamide;

Example 115

2-(1H-indol-6-yl)-N-(6-propoxypyridazin-3-yl)acetamide;

Example 116

2-(1H-indol-6-yl)-N-[6-(4-methylphenoxy)pyridin-3-yl]acetamide;

Example 117

2-(1H-indol-6-yl)-N-[5-(4-methylphenoxy)pyridin-2-yl]acetamide;

Example 118

N(H-indol-6-ylmethyl)-5-methoxypyridine-2-carboxamide;

Example 119

5-ethoxy-N-(1H-indol-6-ylmethyl)pyridine-2-carboxamide;

Example 120

N-(1H-indol-6-ylmethyl)-5-isopropoxypyridine-2-carboxamide;

Example 121

N-(1H-indol-6-ylmethyl)-5-propoxypyridine-2-carboxamide;

Example 122

N-(1H-indol-6-ylmethyl)-5-(trifluoromethoxy)pyridine-2-carboxamide;

Example 123

N-(1H-indol-6-ylmethyl)-5-(2,2,2-trifluoroethoxy)pyridine-2-carboxamide;

Example 124

N-(1H-indol-6-ylmethyl)-5-phenoxypyridine-2-carboxamide;

Example 125

2-(1H-indol-6-yl)-N-(5-isopropoxypyridine-2-yl)acetamide;

Example 126

N-(5-ethoxypyridin-2-yl)-2-(1H-indol-6-yl)acetamide;

Example 127

2-(1H-indol-6-yl)-N-(5-methoxypyridin-2-yl)acetamide;

Example 128

2-(1H-indol-6-yl)-N-(5-propoxypyridin-2-yl)acetamide;

Example 129

2-(1H-indol-6-yl)-N-[5-(trifluoromethoxy)pyridin-2-yl]acetamide;

Example 130

2-(1H-indol-6-yl)-N-[5-(2,2,2-trifluoroethoxy)pyridin-2]acetamide,

Example 131

2-(1H-indol-6-yl)-N-(5-phenoxypyridin-2-yl)acetamide;

Example 132

N-(1H-indol-5-ylmethyl)-6-[(trifluoromethyl)thio]nicotinamide;

Example 133

N-(1H-indol-5-ylmethyl)-5-[(trifluoromethyl)thio]pyridine-2-carboxamide;

Example 134

2-(1H-indol-5-yl)-N-{6-[(trifluoromethyl)thio]pyridin-3-yl}acetamide;

Example 135

2-(1H-indol-5-yl)-N-{5-[(trifluoromethyl)thio]pyridin-2-yl}acetamide;

Example 136

2-(1H-indol-5-yl)-N-{6-[(trifluoromethyl)thio]pyridazin-3-yl}acetamide;

Example 137

N-(1H-indol-5-ylmethyl)-6-phenylnicotinamide;

Example 138

N-(1H-indol-5-ylmethyl)-1,1'-biphenyl-4-carboxamide;

Example 139

N-(1H-indol-5-ylmethyl)-6-phenylpyridazin-3-carboxamide;

Example 140

N-(1H-indol-5-ylmethyl)-5-phenylpyridine-2-carboxamide;

Example 141

2-(1H-indol-5-yl)-N-(6-phenylpyridin-3-yl)acetamide;

Example 142

2-(1H-indol-5-yl)-N-(5-phenylpyridin-2-yl)acetamide;

Example 143

N-1,1'-biphenyl-4-yl-2-(1H-indol-5-yl)acetamide:

Example 144

2-(1H-indol-5-yl)-N-(6-phenylpyridazin-3-yl)acetamide;

Example 145

N-(1H-indol-6-ylmethyl)-6-[(trifluoromethyl)thio]nicotinamide;

Example 146

N-(1H-indol-6-ylmethyl)-5-[(trifluoromethyl)thio]pyridine-2-carboxamide;

Example 147

2-(1H-indol-6-yl)-N-{6-[(trifluoromethyl)thio]pyridin-3-yl}acetamide;

Example 148

2-(1H-indol-6-yl)-N-{5-[(trifluoromethyl)thio]pyridin-2-yl}acetamide;

Example 149

2-(1H-indol-6-yl)-N-{6-[(trifluoromethyl)thio]pyridazin-3-yl}acetamide;

Example 150

N-(1H-indol-6-ylmethyl)-6-phenylnicotinamide;

Example 151

N-(1H-indol-6-ylmethyl)-5-phenylpyridine-2-carboxamide;

Example 152

N-(1H-indol-6-ylmethyl)-6-phenylpyridazin-3-carboxamide;

Example 153

N-(1H-indol-6-ylmethyl)-1,1'-biphenyl-4-carboxamide;

Example 154

2-(1H-indol-6-yl)-N-(6-phenylpyridin-3-yl)acetamide;

Example 155

2-(1H-indol-6-yl)-N-(5-phenylpyridin-2-yl)acetamide;

Example 156

2-(1H-indol-6-yl)-N-(6-phenylpyridazin-3-yl)acetamide;

Example 157

N-1,1'-biphenyl-4-yl-2-(1H-indol-6-yl)acetamide;

Example 158

N-(1H-indol-5-ylmethyl)-4-(trifluoromethyl)benzamide;

Example 159

N-(1H-indol-5-ylmethyl)-5-(trifluoromethyl)pyridine-2-carboxamide;

Example 160

N-(1H-indol-5-ylmethyl)-6-(trifluoromethyl)pyridazine-3-carboxamide;

Example 161

5-chloro-A-(1H-indol-5-ylmethyl)pyridine-2-carboxamide;

Example 162

4-chloro-N-(1H-indol-5-ylmethyl)benzamide;

Example 163

4-cyclopropyl-N-(1H-indol-5-ylmethyl)benzamide;

Example 164

6-cyclopropyl-N-(1H-indol-5-ylmethyl)nicotinamide;

Example 165

5-cyclopropyl-N-(1H-indol-5-ylmethyl)pyridine-2-carboxamide;

Example 166

6-cyclopropyl-N-(1H-indol-5-ylmethyl)pyridazine-3-carboxamide;

Example 167

2-(1H-indol-5-yl)-N-[4-(trifluoromethyl)phenyl]acetamide;

Example 168

2-(1H-indol-5-yl)-N-[5-(trifluoromethyl)pyridin-2-yl]acetamide;

Example 169

2-(1H-indol-5-yl)-N-[6-(trifluoromethyl)pyridazin-3-yl]acetamide;

Example 170

N-(4-cyclopropylphenyl)-2-(1H-indol-5-yl)acetamide;

Example 171

N-(6-cyclopropylpyridin-3-yl)-2-(1H-indol-5-yl)acetamide;

Example 172

N-(5-cyclopropylpyridin-2-yl)-2-(1H-indol-5-yl)acetamide;

Example 173

N-(6-cyclopropylpyridazin-3-yl)-2-(1H-indol-5-yl)acetamide;

Example 174

N-[4-(3-chlorophenoxy)phenyl]-2-(1H-indol-5-yl)acetamide;

Example 175

N-[4-(2,5-dichlorophenoxy)phenyl]-2-(1H-indol-5-yl)acetamide;

Example 176

2-(1H-indol-5-yl)-1-{4-[4-(trifluoromethoxy)phenoxy]phenyl}acetamide;

Example 177

N-[4-(4-chlorophenoxy)phenyl]-2-(1H-indol-5-yl)acetamide;

Example 178

N-[6-(3-chlorophenoxy)pyridin-3-yl]-2-(1H-indol-5-yl)acetamide;

Example 179

N-[6-(2,5-dichlorophenoxy)pyridin-3-yl]-2-(1H-indol-5-yl)acetamide;

Example 180

2-(1H-indol-5-yl)-N-{6-[4-(trifluoromethoxy)phenoxy]pyridin-3-yl}acetamide;

Example 181

N-[6-(4-chlorophenoxy)pyridin-3-yl]-2-(1H-indol-5-yl)acetamide;

Example 182

N-[5-(3-chlorophenoxy)pyridin-2-yl]-2-(1H-indol-5-yl)acetamide;

Example 183

N-[5-(2,5-dichlorophenoxy)pyridin-2-yl]-2-(1H-indol-5-yl)acetamide;

Example 184

2-(1H-indol-5-yl)-N-{5-[4-(trifluoromethoxy)phenoxy]pyridin-2-yl}acetamide;

Example 185

N-[5-(4-chlorophenoxy)pyridin-2-yl]-2-(1H-indol-5-yl)acetamide;

Example 186

2-(1H-indol-5-yl)-N-[6-(phenylthio)pyridin-3-yl]acetamide;

Example 187

N-{6-[(2,5-dichlorophenyl)thio]pyridin-3-yl}-2-(1-indol-5-yl)acetamide;

Example 188

2-(1H-indol-5-yl)-N-(6-{[3-(trifluoromethoxy)phenyl]thio}pyridin-3-yl)acetamide;

Example 189

N-[(2-methyl-1H-indol-5-yl)methyl]-6-(2,2,2-trifluoroethoxy)nicotinamide; and

Example 190

2-(2-methyl-1H-indol-5-yl)-N-[6-(2,2,2-trifluoroethoxy)pyridin-3-yl]acetamide.

Example 191

2-(1H-indol-5-yl)-N-{4-[(trifluoromethyl)thio]phenyl}acetamide

The titled compound was prepared from 4-(trifluoromethylthio)aniline and indole-5-acetic acid (prepared as described in Naruto, S., et al., O. Chem. Pharm. Bull. 1972, 20 (10), 2163-2171) according to method A: $^1$H NMR (300 MHz, DMSO-$d_6$) δ ppm 3.69 (s, 2H), 6.38 (ddd, J=3.0, 1.9, 0.8 Hz, 1H), 7.06 (dd, J=8.3, 1.5 Hz, 1H), 7.30 (t, J=2.8 Hz, 1H), 7.33 (d, J=8.3 Hz, 1H), 7.48 (d, J=0.8 Hz, 1H), 7.60-7.66 (m, 2H), 7.73-7.80 (m, 2H), 10.42 (s, 1H), 11.01 (br s, 1H); MS (DCI/NH$_3$) m/z 368.1 (M+NH4)$^+$, 351.1 (M+H)$^+$.

Example 192

N-{4-[(difluoromethyl)thio]phenyl}-2-(1H-indol-5-yl)acetamide

The titled compound was prepared from 4-(difluoromethylthio)aniline and indole-5-acetic acid according to method A: $^1$H NMR (300 MHz, DMSO-$d_6$) δ ppm 3.68 (s, 2H), 6.38 (ddd, J=3.0, 1.7, 0.7 Hz, 1H), 7.06 (dd, J=8.1, 1.7 Hz, 1H), 7.30 (t, J=2.9 Hz, 1H), 7.37 (t, J=56.1 Hz, 1H), 7.33 (d, J=8.1, 1H), 7.48 (br s, 1H), 7.48-7.54 (m, 2H), 7.66-7.73 (m, 2H), 10.33 (s, 1H) 11.01 (s, 1H); MS (DCI/NH$_3$) m/z 350.1 (M+NH4)$^+$, 333.1 (M+H)$^+$.

Example 193

2-(1H-indol-5-yl)-N-[6-(2,2,2-trifluoroethoxy)pyridin-3-yl]acetamide

The titled compound was prepared from 6-(2,2,2-trifluoroethoxy)pyridin-3-amine and indole-5-acetic acid according to method A: $^1$H NMR (300 MHz, DMSO-$d_6$) δ ppm 3.66 (s, 2H), 4.92 (q, J=9.3 Hz, 1H), 6.38 (ddd, J=3.0, 1.8, 0.7 Hz, 1H), 6.95 (d, J=9.0 Hz, 1H), 7.06 (dd, J=8.3, 1.6 Hz, 1H), 7.30 (t, J=2.9 Hz, 1H), 7.33 (d, J=8.3 Hz, 1H), 7.48 (br s, 1H) 7.99 (dd, J=8.8, 2.8 Hz, 1H), 8.41 (d, J=2.8 Hz, 1H), 10.22 (s, 1H), 11.01 (br s, 1H); MS (DCI/NH$_3$) m/z 350.1 (M+H)$^+$.

Example 194

2-(1H-indol-5-yl)-N-[6-(trifluoromethyl)pyridin-3-yl]acetamide

The titled compound was prepared from 6-(trifluoromethyl)pyridin-3-amine and indole-5-acetic acid according to method A: $^1$H NMR (300 MHz, CD$_3$OD) δ ppm 3.79 (s, 2H), 6.41 (dd, J=3.1, 1.0 Hz, 1H), 7.10 (dd, J=8.5, 1.7 Hz, 1H), 7.21 (d, J=3.1 Hz, 1H), 7.35 (d. J=8.5 Hz, 1H), 7.53 (dd, J=1.7, 0.7 Hz, 1H), 7.74 (d. J=8.8 Hz, 1H), 8.34 (ddd, J=8.6, 2.5, 0.7 Hz, 1H), 8.84 (d, J=2.4 Hz, 1H)); MS (DCI/NH$_3$) m/z 320.1 (M+H)$^+$.

Example 195

2-(1H-indol-5-yl)-N-(4-phenoxyphenyl)acetamide

The titled compound was prepared from 4-(phenoxy)aniline and indole-5-acetic acid according to method A: $^1$H NMR (300 MHz, CD$_3$OD) δ ppm 3.72 (s, 2H), 6.41 (d, J=3.2 Hz, 1H), 6.91-6.94 (m, 2H), 6.92-6.97 (m, 2H), 7.06 (t, J=7.1 Hz, 1H), 7.11 (dd. J=8.5, 1.8 Hz, 1H), 7.21 (d, J=3.2 Hz, 1H), 7.30 (d, J=8.3 Hz, 1H), 7.33-7.38 (m, 2H), 7.48-7.55 (m, 2H), 7.52 (s, 1H)); MS (DCI/NH$_3$) m/z 343.2 (M+H)$^+$.

Example 196

2-(1H-indol-5-yl)-N-{3-[(trifluoromethyl)thio]phenyl}acetamide

The titled compound was prepared from 3-(trifluoromethylthio)aniline and indole-5-acetic acid according to method A: $^1$H NMR (300 MHz, CD$_3$OD) δ ppm 3.75 (s, 2H), 6.41 (dd, J=3.1, 1.0 Hz, 1H), 7.10 (dd, J=8.5, 1.7 Hz, 1H), 7.21 (d, J=3.1 Hz, 1H), 7.35 (d, J=8.1 Hz, 1H), 7.38 (dd, J=7.0, 2.1 Hz, 1H), 7.41 (t, J=7.0 Hz, 1H), 7.53 (dd, J=1.7, 0.7 Hz, 1H), 7.73 (dt, J=7.0, 2.1 Hz, 1H), 8.00 (t, J=2.0 Hz, 1H); MS (DCI/NH$_3$) m/z 368.1 (M+NH4)$^+$ 351.1 (M+H)$^+$.

Example 197

N-(6-chloropyridin-3-yl)-2-(1H-indol-5-yl)acetamide

The titled compound was prepared from 5-amino-2-chloropyridine and indole-5-acetic acid according to method A: $^1$H NMR (300 MHz, CD$_3$OD) δ ppm 3.75 (s, 2H), 6.40 (dd, J=3.1, 1.0 Hz, 1H), 7.09 (dd, J=8.5, 1.7 Hz, 1H), 7.21 (d, J=3.1 Hz, 1H), 7.33 (s, 1H), 7.39 (s, 1H), 7.52 (d, J=1.0 Hz, 1H), 8.09 (dd, J=8.8, 2.7 Hz, 1H), 8.55 (dd, J=2.7, 0.7 Hz, 1H); MS (DCI/NH$_3$) m/z 286.1 (M+H)$^+$.

Example 198

N-(1H-indol-6-ylmethyl)-4-[(trifluoromethyl)thio]benzamide

A suspension of 4-(trifluoromethylthio)benzoic acid (0.333 g, 1.499 mmol; Aldrich) and 1H-indole-6-methanamine (0.146 g, 0.999 mmol; Chemgenix) in 10:1 dichloromethane-N,N-dimethylformamide (16.5 mL) was treated with PS-carbodiimide (1.5 g, 1.875 mmol; Biotage) and stirred at room temperature for 60 hours. The suspension was filtered through diatomaceous earth, rinsing with dichloromethane. The resulting material was purified by flash chromatography (40 g silica gel column, 5-95% gradient of ethyl acetate in hexanes), then purified further by preparative HPLC [Waters 30×100 mm XBridge C18 OBD 5µ column, flow rate 40 ml/minute, 5-95% gradient of acetonitrile in buffer (0.1 M aqueous ammonium bicarbonate, adjusted to pH 10 with ammonium hydroxide)] to afford the title compound: $^1$H NMR (300 MHz, CDCl$_3$) δ ppm 4.74 (d, J=5.4 Hz, 2H), 6.40 (s, 1H), 6.55 (ddd, J=3.1, 2.0, 1.0 Hz, 1H), 7.10 (dd, J=8.1, 1.7 Hz, 1H), 7.20-7.25 (m, 1H), 7.41 (s, 1H), 7.63 (d, J=8.1 Hz, 1H), 7.66-7.73 (m, 2H), 7.81 (dt, J=8.5, 2.0 Hz, 2H), 8.13-8.29 (m, 1H); MS (+DCI) m/z 351 (M+H)$^+$, 368 (M+NH$_4$)$^+$.

Example 199

N-(1H-indol-6-ylmethyl)-6-(trifluoromethyl)nicotinamide

The titled compound was prepared from 6-(trifluoromethyl)nicotinic acid (0.286 g, 1.498 mmol; Matrix) and 1H-indole-6-methanamine (0.146 g, 0.999 mmol; Chemgenix) using the procedure in Example 198: $^1$H NMR (300 MHz, CDCl$_3$) δ ppm 4.77 (d, J=5.2 Hz, 2H), 6.39-6.51 (br s, 1H), 6.56 (d, J=3.2 Hz, 1H), 7.11 (dd, J=8.1, 1.4 Hz, 1H) 7.22-7.26 (m, 1H), 7.43 (s, 1H), 7.65 (d, J=8.3 Hz, 1H), 7.76 (d, J=8.3 Hz, 1H) 8.13-8.26 (br s, 1H), 8.30 (dd, J=8.1, 2.2 Hz, 1H), 9.06 (d, J=2.0 Hz, 1H-1); MS (+DCI) m/z 320 (M+H)$^+$, 337 (M+NH$_4$)$^+$.

Determination of Biological Activity

To determine the effectiveness of compounds of formula (I), formula (II), or formula (III), as allosteric modulators, the compounds of the invention were evaluated according to the following assays. These include (i) *Xenopus* oocytes injected with α7 NNR RNA or DNA and evaluation of compound effects on current responses evoked by acetylcholine or another agonist (ii) IMR-32 cells endogenously expressing α7 NNRs and measuring Ca$^{2+}$ flux or membrane potential changes utilizing the fluorescence-imaging plate reader (FLIPR)-based assays and (iii) measurement of phospho-ERK activity using western blot assays. These assays allow for evaluation of allosteric modulators using *Xenopus* oocytes, cells or cell lines expressing endogenous or recombinant α7 NNRs.

To determine the effectiveness of compounds of formula (I), formula (II), or formula (III) in reducing pain, the compounds of the invention were evaluated in the formalin-induced persistent nociceptive behavior assay.

(i) Two-Electrode Voltage-Clamp in *Xenopus laevis* Oocytes

Figure 2:
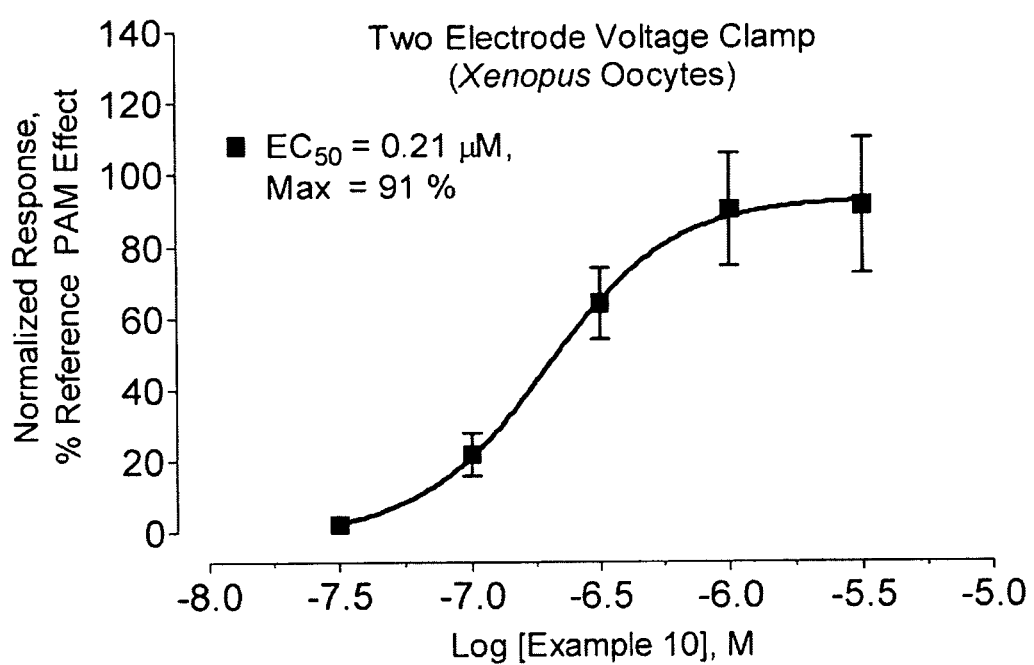
FIG. 2 is a concentration response curve obtained in the same manner for a PAM (Example 10). The response obtained by submaximum ACh in the presence of the reference PAM at 10 μM (N'-[(2Z)-3-(2,2-difluoro-1,3-benzodioxol-5-yl)-5-methyl-1,3-thiazol-2(3H)-ylidene]-N,N-dimethylurea) is considered as 100% and the response of submaximum ACh without any PAM as 0%. Normalized PAM potentiation is plotted on the Y-axis as a function of the concentration of the test modulator (depicted along the X-axis).
Figure 3:
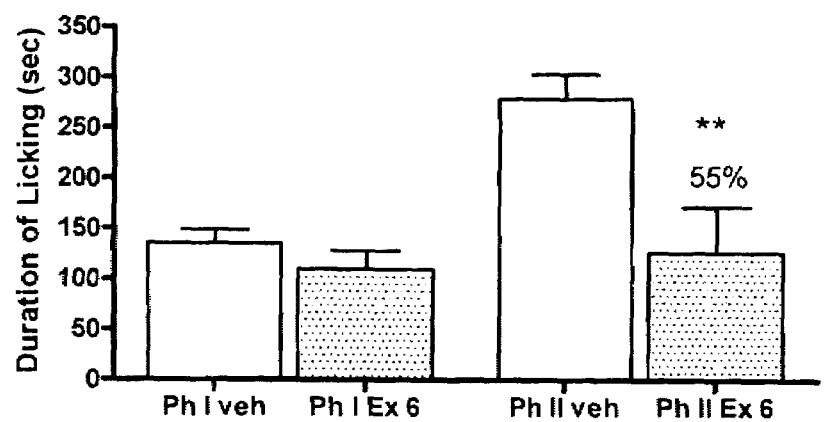
FIG. 3 is a graphical representation of nocifensive response (licking duration) following treatment with vehicle or a PAM (Example 6) followed by exposure to formalin in mice. In Phase I (0-5 minutes post formalin injection) there is no significant difference in response. In Phase II (20-45 minutes post formalin injection) a significant reduction (55%) in licking behavior was observed, indicative of pain relief in this time period.

*X. laevis* oocytes were prepared for electrophysiological experiments as described in the literature (see for example, Briggs. C. A., et al., *Neutropharmacology*, 1995, 34: 583-590; Briggs, C. A. et al., *Neutropharmacology*, 1998, 37: 1095-1102). In brief, three to four lobes from ovaries of female adult *X. laevis* frogs were removed and defolliculated after treatment with collagenase type IA (2 mg/mL; Sigma) prepared in low-Ca$^{2+}$ Barth's solution (90 mM NaCl, 1.0 mM KCl, 0.66 mM NaNO$_3$, 2.4 mM NaHCO$_3$, 10 mM H-IEPES, 2.5 mM sodium pyruvate, 0.82 mM MgCl$_2$, and 0.5% (v/v) penicillin-streptomycin solution, pH=7.55, Sigma) for about 1.5 hours to about 2 hours at about 18° C. under constant agitation to obtain isolated oocytes. The oocytes were injected with about 4 ng to about 6 ng of human α7 NNR cRNA, kept at about 18° C. in a humidified incubator in modified Barth's solution (90 mM NaCl, 1.0 mM KCl, 0.66 mM NaNO$_3$, 2.4 mM NaHCO$_3$, 10 mM HEPES, 2.5 mM sodium pyruvate, 0.74 mM CaCl$_2$, 0.82 mM MgCl$_2$, 0.5% (v/v) penicillin-streptomycin solution, pH 7.55) and used about 2 to 7 days after injection. Responses were measured by two-electrode voltage clamp using a parallel oocyte electrophysiology test station (Abbott, Abbott Park, Ill.) (see for example, Trimbull, J. D., Maslana, E. S., McKenna, D. G., Nemcek, T. A., Niforatos, W., Pan, J. Y., Parihar, A. S., Shieh, C. C., Wilkins, J. A., Briggs, C. A., and Bertrand, D. High throughput electrophysiology using a fully automated, multiplexed recording system, *Receptors Channels*, 2003, 9: 19-28). During recordings, the oocytes were bathed in Ba$^{2+}$—OR2 solution (90 mM NaCl, 2.5 mM KCl, 2.5 mM BaCl$_2$, 1.0 mM MgCl$_2$, 5.0 mM HEPES, and 0.0005 mM atropine, pH 7.4) to prevent activation of Ca$^{2+}$-dependent currents and held at −60 mV at room temperature (about 20° C.). Test compounds were given for ~60 seconds before agonist application and subsequently in the presence of 0.1 mM ACh. The data were expressed as percentage potentiation normalized to the reference PAM (at 10 µM, N'-[(2Z)-3-(2,2-difluoro-1,3-benzodioxol-5-yl)-5-methyl-1,3-thiazol-2(3H)-ylidene]-N,N-dimethylurea) taken as 100% and the response to submaximum ACh without any PAM as 0%. FIG. 1 shows the concentration-response relationship for Example 12 in potentiating 0.1 mM ACh-evoked α7 currents in oocytes. In this graph, the $EC_{50}$ value is 1.1 μM and the degree of potentiation is 99%. FIG. 2 shows the concentration-response relationship for Example 10 in potentiating 0.1 mM ACh-evoked α7 currents in oocytes. In this graph, the $EC_{50}$ value is 0.21 μM and the degree of potentiation is 91%.

(ii) High-Throughput Calcium Flux Assays Using Cells Expressing Endogenous α7 NNRs Since allosteric modulators affect the kinetics of channel function and thus affect calcium dynamics, it is demonstrated that novel modulators can be identified when assays are conducted in the presence of a selective agonist, and conversely, novel agonists can be identified when screened or tested in the presence an allosteric modulator. As such, PAMs and nicotinic acetylcholine receptor agonists can be identified by using IMR-32 cells that endogenously express various nicotinic receptors including α7 NNRs. It is contemplated that such assay can be utilized with a number of cell lines conventionally not amenable to α7 nicotinic compound screening. Accordingly, allosteric modulator compounds described herein can be identified using a fluorescence-based throughput functional assay using cell lines such as IMR-32 neuroblastoma or primary dissociated neurons. Although cell types such as IMR-32 neuroblastoma and neurons are known to contain several nicotinic receptor subunits, α7 selective agonists in the present assay selectively stimulate calcium responses only in the presence of PAMS. Any suitable selective α7 agonist can be used. Selective α7 agonists from a range of structural types may be used such as those described in the literature including PNU-282987, SSR180711A and AR-R17779, and others described in earlier patent applications, such as 2-methyl-5-(6-phenyl-pyridazin-3-yl)-octahydro-pyrrolo[3,4-c]pyrrole (see for example, US 20050065178), 5-[6-(5-methyl-hexahydro-pyrrolo[3,4-c]pyrrol-2yl)-pyridazin-3-yl]-1H-indole (see for example, US 20050065178), 3-[6-(1H-indol-5-yl)-pyridazin-3-yloxy]-1-aza-bicyclo[2.2.2]octanie (see for example, US 2005/0137204 and US 2005/0245531), and 4-(5-phenyl-[1,3,4]oxadiazol-2-yl)-1,4-diaza-bicyclo[3.2.2]nonane (see for example, WO 2004/029053).

IMR-32 neuroblastoma cells (ATCC) were grown to confluency in 162 cm² tissue culture flasks in minimum essential media supplemented with 10% FBS and 1 mM sodium pyruvate, 0.1 mM non-essential amino acids and 1% antibiotic-antimycotic. The cells were then dissociated using cell dissociation buffer and 100 μL of 3.5×10⁵ cells/mL cell suspension was plated (about 75,000-100,000 cells/well) into black 96 well plates precoated with poly-D-lysine with a clear bottom and maintained for 24-48 hours in a tissue culture incubator at 37° C. under an atmosphere of 5% $CO_2$: 95% air. Other clonal cell lines or dissociated primary cortical neurons that express endogenous α7 nicotinic receptors may also be used in this assay. Calcium flux was measured using a calcium-3 assay kit (Molecular Devices, Sunnyvale, Calif.) or fluo-4. A stock solution of the dye was prepared by dissolving each vial supplied by the vendor in Hank's balanced salt solution buffer (HBSS) containing 10 or 20 mM HEPES. The stock solution was diluted 1:20 using the same buffer before use. The growth media was removed from the cells and loaded with 100 μL of the dye and incubated at room temperature for one to three hours. Fluorescence measurements were read simultaneously from all the wells by a Fluorometric Imaging Plate Reader (FLIPR) at an excitation wavelength of 480 nm and an emission wavelength of 520 nm. Baseline fluorescence was measured for the first 10 seconds at which 50 μL of 3× concentrations of modulator/test compounds were added to the cell plate and incubated for three to five minutes. The fluorescence intensity was captured every second for the first 1 minute followed by every 2-5 seconds for an additional two to four minutes. This procedure was followed by 50 μl, of 4× concentration of agonist and readings were taken for a period of three to five minutes as described above. The assay can also be adapted to other formats such as 384- or 1536-well formats. Data were plotted as a function of concentration and normalized to the response of the reference PAM (10 μM N'-[(2Z)-3-(2,2-difluoro-1,3-benzodioxol-5-yl)-5-methyl-1,3-thiazol-2(3H)-ylidene]-N,N-dimethylurea). The concentration dependence of changes in fluorescence responses was fitted by nonlinear regression analysis (GraphPad Prism, San Diego, Calif.) or Assay Explorer (Elsevier MDL, San Ramon, Calif.) to obtain $EC_{50}$ values. Agonist alone did not evoke any responses. However, in the presence of an allosteric modulator, the agonist elicited a concentration dependent increase in calcium response. The α7 selective antagonist, methyllycaconitine (MLA), abolished the response demonstrating that the effects are mediated via the α7 receptor.

PAMs were identified by measuring fluorescence changes to intracellular calcium in a fluorometric plate reader in the presence of a selective α7 NNR agonist using cells natively expressing α7 NNRs. Compounds with PAM activity evoked a calcium fluorescence response in the IMR-32 neuroblastoma cell line, a cell line that expresses endogenous α7 NNRs when the assay is conducted in presence of an α7 NNR agonist. The agonist alone did not evoke a calcium response. However, when the agonist and the modulator were co-applied together, calcium responses were triggered. In the example above, 4-(5-phenyl-[1,3,4]oxadiazol-2-yl)-1,4-diaza-bicyclo[3.2.2]nonane (see for example, WO 2004/029053) was used as an agonist at 1 μM in the presence of varying concentrations of compounds of the invention. The $EC_{50}$ values of PAM compounds as determined in this assay typically can range from 1 nM to >30 μM. Other α7 agonists including 2-methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c]pyrrol-2yl)-pyridazin-3-yl]-1H-indole (published in US 20050065178), various quinuclidine derivatives (see for example, US 2005/0137204 and US 2005/0245531) and PNU-282987 (see for example, Hajós, M., et al., *J Pharmacol. Exp Ther.*, 2005, 312: 1213-22) also are suitable for the assay. Likewise, primary neurons and other clonal cell lines that natively express α7 NNRs may also be utilized. Other fluorescence measurements such as those monitoring changes in membrane potential also are suitable for the assay.

(iii) High-Throughput ERK Phosphorylation Assays Using Cells Expressing Endogenous α7 NNRs Rat pheochromocytoma (PC-12) cells (ATCC, Manassas, Va.) were cultured and maintained in F-12K media supplemented with 15% horse serum, 2.5% fetal calf serum, and 2 mM L-glutamine in poly-D lysine coated dishes at 37° C. and 5% $CO_2$. Cells were plated in black-walled clear bottom 96-well Biocoat™ plates coated with poly-D-lysine (BD Biosciences, Bedford, Mass.) and grown for 2-3 days. Afterward, the culture media is replaced with serum-free media to starve cells overnight. On the day of the assay, cell media was removed and cells (60-80% confluent) were treated with agonist and/or modulator in Dulbecco's phosphate buffer saline (D-PBS) (with $Ca^{2+}$, $Mg^{2+}$, and 1 mg/mL D-glucose).

PC-12 cells are treated for 10 minutes at 37° C. with test PAM compounds and then challenged with a selective α7 agonist for 5 minutes at 37° C. in a final volume of 100 μL/well, unless otherwise indicated. After treatment, media was discarded and adherent cells were immediately fixed in the presence of 150 μL/well of 3.7% formaldehyde/phosphate-buffered saline for 30-60 minutes at room temperature. Cells were then washed (4 times/5 minutes) and permeabilized with 200 μL/well of 0.1% Triton X-100/PBS. Permeabilized cells were blocked using the Odyssey® blocking buffer (100 μL/well) and plates were rocked overnight at 4° C. Both anti-total ERK (rabbit) and anti-phospho ERK (mouse) antibodies were diluted to 1/1000 and 1/500, respectively, in Odyssey® blocking buffer and added together at 50 μL/well for 2-3 hours at room temperature. Polyclonal rabbit anti-ERK1/2 and monoclonal mouse anti-phospho-ERK 1/2 were purchased from Sigma-Aldrich (St. Louis, Mo.). The plates were washed 4 times with 0.1% Tween 20/PBS (200 μL/well), and incubated with secondary antibodies (1/1000 dilution) in blocking buffer supplemented with 0.2% Tween for 1 hour. Alexa Fluor® 680-labeled goat anti-rabbit antibodies were added to recognize total ERK labeling (red color) and IRDye™800-labeled donkey anti-mouse antibodies were added to recognize phospho-ERK labeling (green color). Alexa Fluor® 680-labeled goat-anti-rabbit antibodies were obtained from Molecular Probes (Eugene, Oreg.). IRDye™ 800CW-labeled donkey-anti-mouse antibodies were purchased from Rockland (Gilbertsville, Pa.). The plates were washed 4 times with 0.2% Tween and 0.01% SDS/PBS and scanned using the Odyssey® infrared scanner. Well intensities were quantitated and phospho-ERK signals were normalized to total ERK signals by the Odyssey® software. Data analysis was performed using GraphPad Prism (GraphPad Software, San Diego, Calif.).

PAMs can be identified by measuring changes in the phosphorylation of ERK (extracellular receptor kinase) by in-cell western analysis. Compounds with allosteric modulator activity evoke concentration-dependent increases in ERK phosphorylation. To obtain data, an α7 NNR agonist such as PNU-282987 (see for example, Hajos et al., *J. Pharmacol. Exp Ther.* 2005; 312: 1213-22) was used as the α7 selective agonist. Typical $EC_{50}$ values in this assay range from about 10 nM to about 30 μM. Other α7 nicotinic receptor agonists including 2-methyl-5-(6-phenyl-pyridazin-3-yl)-octahydro-pyrrolo[3,4-c]pyrrole, 5-[6-(5-methyl-hexahydro-pyrrolo[3,4-c]pyrrol-2-yl)-pyridazin-3-yl]-1H-indole (published in US 20050065178), various quinuclidine derivatives (see for example, US 2005/0137204 and US 2005/0245531) and 4-(5-Phenyl-[1,3,4]oxadiazol-2-yl)-1,4-diaza-bicyclo[3.2.2] nonane and related analogs (see for example, WO 2004/029053) also are suitable for the assay.

Compounds of the invention are PAMs of α7 NNR that can enhance the effects of a naturally occurring neurotransmitter, acetylcholine, or exogenously administered agonist. Although not being limited by theory, PAMs generally amplify agonist (acetylcholine) responses by (i) attenuating receptor desensitization so that the receptor remains open for longer duration and/or (ii) by directly amplifying the efficacy of ACh by enhancing maximal receptor activation. In either case, such compounds typically boost endogenous transmission of acetylcholine, and can do so in a temporally and spatially restricted manner since these effects will be localized to regions where the α7 receptors are expressed. Allosteric modulator compounds can modulate the function of α7 NNRs by enhancing ion channel function as measured by calcium responses described herein, or other approaches such as current or membrane potential studies. Preferred compounds are those that behave as PAMs in these assays between a concentration range of about 0.1 nM to about 10 μM. Allosteric modulation of the α7 receptor can trigger key signaling processes that are important to effects on memory, cytoprotection, gene transcription and disease modification. Therefore, the administration of a therapeutically effective amount of a compound of formula (I), formula (II), or formula (III) to a mammal provides a method of selectively modulating the effects of α7 NNRs.

(iv) Formalin-Induced Persistent Nociceptive Behavior Assay

Nociception was assessed using the formalin test. The mice were placed in open plexiglass observation chambers for 30 minutes to allow them to acclimate to their surroundings; then they were removed for formalin administration. Mice were gently restrained while the dorsum of the hind paw was injected with 20 μL of 2.5% formalin into the plantar surface of the right hind paw with a 30-gauge needle. The animals were returned to the chambers and nociceptive behavior was observed immediately after formalin injection. Mirrors were placed in each chamber to enable unhindered observation. Nociceptive behavior was quantified as the time licking the injected paw for continuous 5 minutes (phase I) and 20-45 minutes (phase II), following formalin injection. Formalin-induced flinching/licking behavior was biphasic. The initial acute phase (phase I, 0-5 minutes) was followed by a relatively short quiescent period, which was then followed by a prolonged tonic response (phase II, 20-45 minutes).

A reference PAM compound (N-(1H-indol-5-ylmethyl)-6-(2,2,2-trifluoroethoxy)nicotinamide at 10 mg/kg in 10% DMSO/HBC) administered subcutaneously 10 minutes prior to formalin injection has no anti-nociceptive activity observed in phase I, but reduced nociceptive behaviors of injected paw flicking duration by 55%, indicative of pain relief in this time period as shown in Scheme 3 indicating that the PAM compound might have inhibitory effect on formalin-induced central neuronal sensitization.

It is understood that the foregoing detailed description and examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (III):

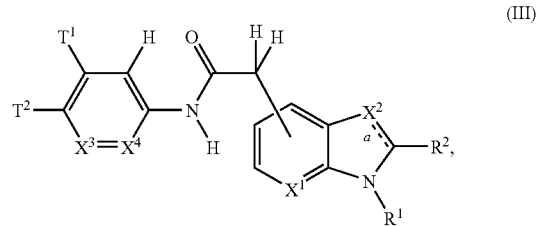

wherein
$R^1$ is alkylcarbonyl, hydrogen, or methyl;
$R^2$ is hydrogen or methyl;
a is a single or double bond;
$X^1$ is N or CH;
$X^2$ is CH when a is a double bond, and $X^2$ is $CH_2$ or —$CH_2CH_2$— when a is a single bond;
$X^3$ and $X^4$ are independently N or CH;

T¹ and T² are independently hydrogen, alkyl, aryl, cycloalkyl, halo, haloalkyl, or R³-L²-, wherein at least one of T¹ and T² is other than hydrogen;

L² is O or S; and

R³ is alkyl, aryl, cycloalkyl, or haloalkyl;

or a pharmaceutically acceptable salt, ester, or amide thereof.

2. The compound of claim 1, selected from the group consisting of:

2-(1H-indol-5-yl)-N-[6-(2,2,2-trifluoroethoxy)pyridin-3-yl]acetamide;
N-{4-[(difluoromethyl)thio]phenyl}-2-(1H-indol-5-yl)acetamide;
2-(1H-indol-5-yl)-N-(4-isopropoxyphenyl)acetamide;
N-(4-ethoxyphenyl)-2-(1H-indol-5-yl)acetamide;
2-(1H-indol-5-yl)-N-(4-methoxyphenyl)acetamide;
2-(1H-indol-5-yl)-N-(4-propoxyphenyl)acetamide;
2-(1H-indol-5-yl)-N-[4-(trifluoromethoxy)phenyl]acetamide;
2-(1H-indol-5-yl)-N-[4-(2,2,2-trifluoroethoxy)phenyl]acetamide;
2-(1H-indol-5-yl)-N-(6-isopropoxypyridin-3-yl)acetamide;
N-(6-ethoxypyridin-3-yl)-2-(1H-indol-5-yl)acetamide;
2-(1H-indol-5-yl)-N-(6-methoxypyridin-3-yl)acetamide;
2-(1H-indol-5-yl)-N-(6-propoxypyridin-3-yl)acetamide;
2-(1H-indol-5-yl)-N-[6-(trifluoromethoxy)pyridin-3-yl]acetamide;
2-(1H-indol-5-yl)-N-[6-(2,2,2-trifluoroethoxy)pyridin-3-yl]acetamide;
2-(1H-indol-5-yl)-N-(6-phenoxypyridin-3-yl)acetamide;
2-(1H-indol-5-yl)-N-(6-isopropoxypyridazin-3-yl)acetamide;
N-(6-ethoxypyridazin-3-yl)-2-(1H-indol-5-yl)acetamide;
2-(1H-indol-5-yl)-N-(6-methoxypyridazin-3-yl)acetamide;
2-(1H-indol-5-yl)-N-(6-propoxypyridazin-3-yl)acetamide;
2-(1H-indol-5-yl)-N-[6-(4-methylphenoxy)pyridin-3-yl]acetamide;
2-(1H-indol-5-yl)-N-[5-(4-methylphenoxy)pyridin-2-yl]acetamide;
2-(1H-indol-5-yl)-N-(5-isopropoxypyridin-2-yl)acetamide;
N-(5-ethoxypyridin-2-yl)-2-(1H-indol-5-yl)acetamide;
2-(1H-indol-5-yl)-N-(5-methoxypyridin-2-yl)acetamide;
2-(1H-indol-5-yl)-N-(5-propoxypyridin-2-yl)acetamide;
2-(1H-indol-5-yl)-N-[5-(trifluoromethoxy)pyridin-2-yl]acetamide;
2-(1H-indol-5-yl)-N-[5-(2,2,2-trifluoroethoxy)pyridin-2-yl]acetamide;
2-(1H-indol-5-yl)-N-(5-phenoxypyridin-2-yl)acetamide;
2-(1H-indol-6-yl)-N-(4-isopropoxyphenyl)acetamide;
N-(4-ethoxyphenyl)-2-(1H-indol-6-yl)acetamide;
2-(1H-indol-6-yl)-N-(4-methoxyphenyl)acetamide;
2-(1H-indol-6-yl)-N-(4-propoxyphenyl)acetamide;
2-(1H-indol-6-yl)-N-[4-(trifluoromethoxy)phenyl]acetamide;
2-(1H-indol-6-yl)-N-[4-(2,2,2-trifluoroethoxy)phenyl]acetamide;
2-(1H-indol-6-yl)-N-(6-isopropoxypyridin-3-yl)acetamide;
N-(6-ethoxypyridin-3-yl)-2-(1H-indol-6-yl)acetamide;
2-(1H-indol-6-yl)-N-(6-methoxypyridin-3-yl)acetamide;
2-(1H-indol-6-yl)-N-(6-propoxypyridin-3-yl)acetamide;
2-(1H-indol-6-yl)-N-[6-(trifluoromethoxy)pyridin-3-yl]acetamide;
2-(1H-indol-6-yl)-N-[6-(2,2,2-trifluoroethoxy)pyridin-3-yl]acetamide;
2-(1H-indol-6-yl)-N-(6-phenoxypyridin-3-yl)acetamide;
2-(1H-indol-6-yl)-N-(6-isopropoxypyridazin-3-yl)acetamide;
N-(6-ethoxypyridazin-3-yl)-2-(1H-indol-6-yl)acetamide;
2-(1H-indol-6-yl)-N-(6-methoxypyridazin-3-yl)acetamide;
2-(1H-indol-6-yl)-N-(6-propoxypyridazin-3-yl)acetamide;
2-(1H-indol-6-yl)-N-[6-(4-methylphenoxy)pyridin-3-yl]acetamide;
2-(1H-indol-6-yl)-N-[5-(4-methylphenoxy)pyridin-2-yl]acetamide;
2-(1H-indol-6-yl)-N-(5-isopropoxypyridin-2-yl)acetamide;
N-(5-ethoxypyridin-2-yl)-2-(1H-indol-6-yl)acetamide;
2-(1H-indol-6-yl)-N-(5-methoxypyridin-2-yl)acetamide;
2-(1H-indol-6-yl)-N-(5-propoxypyridin-2-yl)acetamide;
2-(1H-indol-6-yl)-N-[5-(trifluoromethoxy)pyridin-2-yl]acetamide;
2-(1H-indol-6-yl)-N-[5-(2,2,2-trifluoroethoxy)pyridin-2-yl]acetamide;
2-(1H-indol-6-yl)-N-(5-phenoxypyridin-2-yl)acetamide;
N-(1H-indol-5-ylmethyl)-5-[(trifluoromethyl)thio]pyridine-2-carboxamide;
2-(1H-indol-5-yl)-N-{6-[(trifluoromethyl)thio]pyridin-3-yl}acetamide;
2-(1H-indol-5-yl)-N-{5-[(trifluoromethyl)thio]pyridin-2-yl}acetamide;
2-(1H-indol-5-yl)-N-{6-[(trifluoromethyl)thio]pyridazin-3-yl}acetamide;
2-(1H-indol-5-yl)-N-(6-phenylpyridin-3-yl)acetamide;
2-(1H-indol-5-yl)-N-(5-phenylpyridin-2-yl)acetamide;
N-1,1'-biphenyl-4-yl-2-(1H-indol-5-yl)acetamide;
2-(1H-indol-5-yl)-N-(6-phenylpyridazin-3-yl)acetamide;
2-(1H-indol-6-yl)-N-{6-[(trifluoromethyl)thio]pyridin-3-yl}acetamide;
2-(1H-indol-6-yl)-N-{5-[(trifluoromethyl)thio]pyridin-2-yl}acetamide;
2-(1H-indol-6-yl)-N-{6-[(trifluoromethyl)thio]pyridazin-3-yl}acetamide;
2-(1H-indol-6-yl)-N-(6-phenylpyridin-3-yl)acetamide;
2-(1H-indol-6-yl)-N-(5-phenylpyridin-2-yl)acetamide;
2-(1H-indol-6-yl)-N-(6-phenylpyridazin-3-yl)acetamide;
N-1,1'-biphenyl-4-yl-2-(1H-indol-6-yl)acetamide;
2-(1H-indol-5-yl)-N-[4-(trifluoromethyl)phenyl]acetamide;
2-(1H-indol-5-yl)-N-[5-(trifluoromethyl)pyridin-2-yl]acetamide;
2-(1H-indol-5-yl)-N-[6-(trifluoromethyl)pyridazin-3-yl]acetamide;
N-(4-cyclopropylphenyl)-2-(1H-indol-5-yl)acetamide;
N-(6-cyclopropylpyridin-3-yl)-2-(1H-indol-5-yl)acetamide;
N-(5-cyclopropylpyridin-2-yl)-2-(1H-indol-5-yl)acetamide;
N-(6-cyclopropylpyridazin-3-yl)-2-(1H-indol-5-yl)acetamide;
N-[4-(3-chlorophenoxy)phenyl]-2-(1H-indol-5-yl)acetamide;
N-[4-(2,5-dichlorophenoxy)phenyl]-2-(1H-indol-5-yl)acetamide;
2-(1H-indol-5-yl)-N-{4-[4-(trifluoromethoxy)phenoxy]phenyl}acetamide;
N-[4-(4-chlorophenoxy)phenyl]-2-(1H-indol-5-yl)acetamide;

N-[6-(3-chlorophenoxy)pyridin-3-yl]-2-(1H-indol-5-yl)acetamide;
N-[6-(2,5-dichlorophenoxy)pyridin-3-yl]-2-(1H-indol-5-yl)acetamide;
2-(1H-indol-5-yl)-N-{6-[4-(trifluoromethoxy)phenoxy]pyridin-3-yl}acetamide;
N-[6-(4-chlorophenoxy)pyridin-3-yl]-2-(1H-indol-5-yl)acetamide;
N-[5-(3-chlorophenoxy)pyridin-2-yl]-2-(1H-indol-5-yl)acetamide;
N-[5-(2,5-dichlorophenoxy)pyridin-2-yl]-2-(1H-indol-5-yl)acetamide;
2-(1H-indol-5-yl)-N-{5-[4-(trifluoromethoxy)phenoxy]pyridin-2-yl}acetamide;
N-[5-(4-chlorophenoxy)pyridin-2-yl]-2-(1H-indol-5-yl)acetamide;
2-(1H-indol-5-yl)-N-[6-(phenylthio)pyridin-3-yl]acetamide;
N-{6-[(2,5-dichlorophenyl)thio]pyridin-3-yl}-2-(1H-indol-5-yl)acetamide;
2-(1H-indol-5-yl)-N-(6-{[3-(trifluoromethoxy)phenyl]thio}pyridin-3-yl)acetamide;
2-(2-methyl-1H-indol-5-yl)-N-[6-(2,2,2-trifluoroethoxy)pyridin-3-yl]acetamide;
2-(1H-indol-5-yl)-N-{4-[(trifluoromethyl)thio]phenyl}acetamide;
N-{4-[(difluoromethyl)thio]phenyl}-2-(1H-indol-5-yl)acetamide;
2-(1H-indol-5-yl)-N-[6-(2,2,2-trifluoroethoxy)pyridin-3-yl]acetamide;
2-(1H-indol-5-yl)-N-[6-(trifluoromethyl)pyridin-3-yl]acetamide;
2-(1H-indol-5-yl)-N-(4-phenoxyphenyl)acetamide;
2-(1H-indol-5-yl)-N-{3-[(trifluoromethyl)thio]phenyl}acetamide; and
N-(6-chloropyridin-3-yl)-2-(1H-indol-5-yl)acetamide;
or a pharmaceutically acceptable salt, ester, or amide thereof.

3. A compound selected from N-[(1-acetyl-1H-indol-5-yl)methyl]-6-(2,2,2-trifluoroethoxy)nicotinamide or N-[(1-acetyl-2,3-dihydro-1H-indol-5-yl)methyl]-4-[(trifluoromethyl)thio]benzamide.

4. A pharmaceutical composition comprising a therapeutically effective amount of the compound of formula (III) as in claim 1 in combination with a pharmaceutically acceptable carrier.

5. A method of identifying an α7 NNR agonist comprising allowing the compound of formula (III) as in claim 1 to interact with cells or cell lines endogenously expressing α7 NNRs or cells expressing recombinant α7 NNRs in a fluorescent medium and measuring changes in such fluorescence.

* * * * *